(12) United States Patent
Sutton et al.

(10) Patent No.: US 8,829,194 B2
(45) Date of Patent: Sep. 9, 2014

(54) CRYSTALLINE FORMS OF THE SODIUM SALT OF (4-{4-[5-(6-TRIFLUOROMETHYL-PYRIDIN-3-YLAMINO)-PYRIDIN-2-YL]-PHENYL}-CYCLOHEXYL)-ACETIC ACID

(75) Inventors: Paul Allen Sutton, Parsippany, NJ (US); Michael J. Girgis, Montville, NJ (US); Jessica Liang, Annandale, NJ (US); Mahavir Prashad, Montville, NJ (US); Edwin Bernard Villhauer, Morristown, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/876,063

(22) PCT Filed: Oct. 5, 2011

(86) PCT No.: PCT/US2011/054841
§ 371 (c)(1),
(2), (4) Date: Mar. 26, 2013

(87) PCT Pub. No.: WO2012/047948
PCT Pub. Date: Apr. 12, 2012

(65) Prior Publication Data
US 2013/0184311 A1 Jul. 18, 2013

Related U.S. Application Data

(60) Provisional application No. 61/390,888, filed on Oct. 7, 2010.

(51) Int. Cl.
*C07D 213/04* (2006.01)
*A61K 31/44* (2006.01)
*A61K 31/444* (2006.01)
*C07D 213/72* (2006.01)
*A61K 45/06* (2006.01)
*C07D 401/12* (2006.01)

(52) U.S. Cl.
CPC .......... *C07D 213/72* (2013.01); *A61K 31/444* (2013.01); *A61K 45/06* (2013.01); *C07D 401/12* (2013.01)
USPC .......................................... 546/255; 514/332

(58) Field of Classification Search
CPC ......................... C07D 213/72; C07D 401/12
See application file for complete search history.

(56) References Cited

FOREIGN PATENT DOCUMENTS

WO 2005/102295 A1 11/2005
WO 2007/126957 A2 11/2007

OTHER PUBLICATIONS

Devita, R. et al. J Med Chem 2013 vol. 56 pp. 9820-9825.*
Brittain, ed Polymorphism in Pharmaceutical Solids 2009 pp. 318-335.*
Ivanisevic Pharm Form Qual 2011, pp. 32-33.*

* cited by examiner

*Primary Examiner* — Heidi Reese
(74) *Attorney, Agent, or Firm* — Lisa Matovcik

(57) ABSTRACT

The present invention relates to novel crystalline forms of (4-{4-[5-(6-Trifluoromethyl-pyridin-3-ylamino)-pyridin-2-yl]-phenyl}-cyclohexyl)-acetic acid, sodium and their use in the treatment or prevention of a condition or a disorder associated with DGAT1 activity in animals, particularly humans. It also relates to processes for making such novel crystalline forms.

17 Claims, 13 Drawing Sheets

Figure 1    Sorption results of Modification A
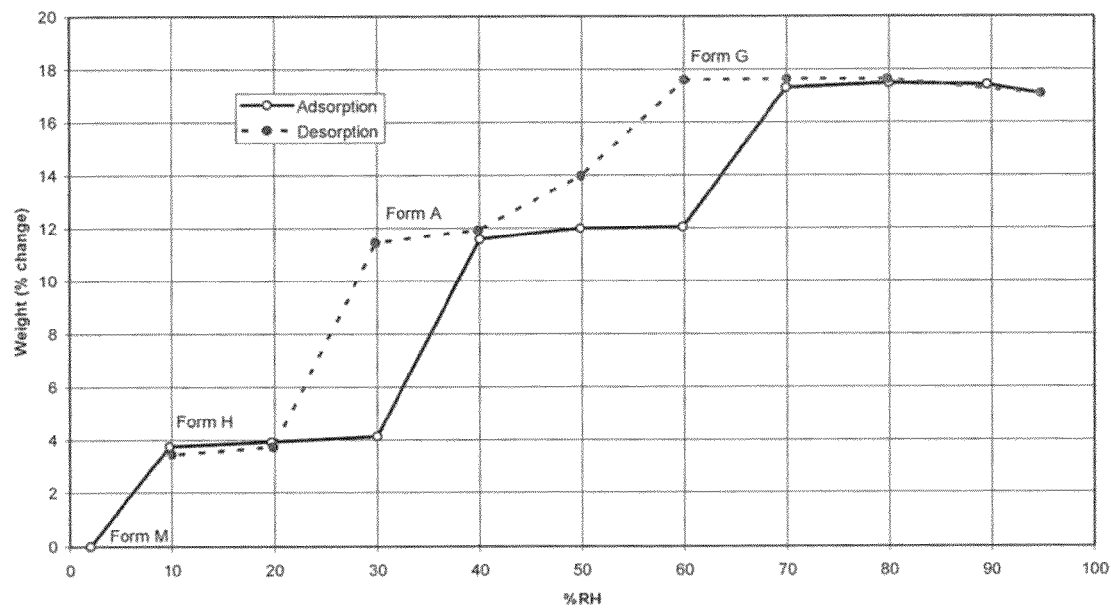

Figure 2.1 X-ray Powder Diffraction Pattern (PXRD) of Modification A
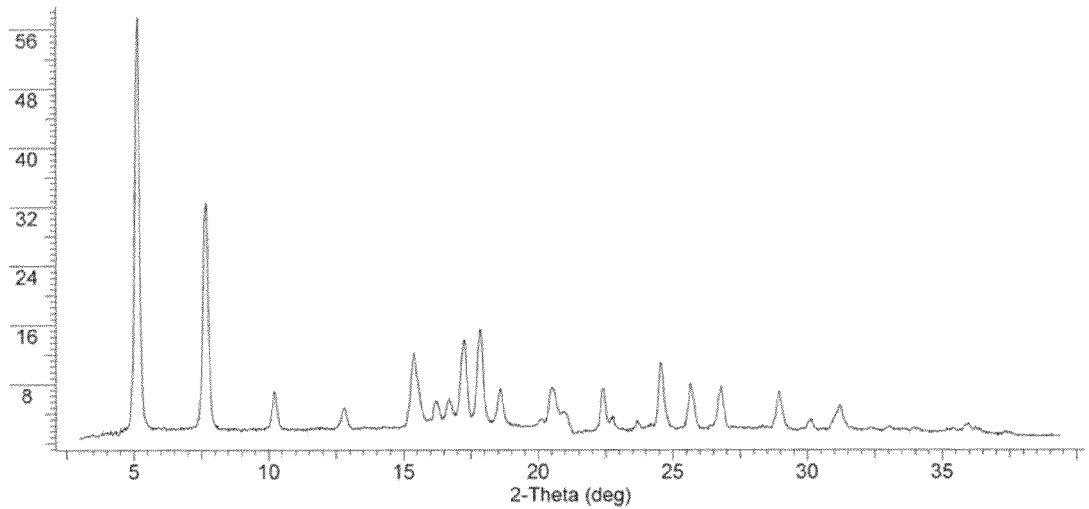
Figure 2.2: X-ray Powder Diffraction Pattern (PXRD) of Modification B
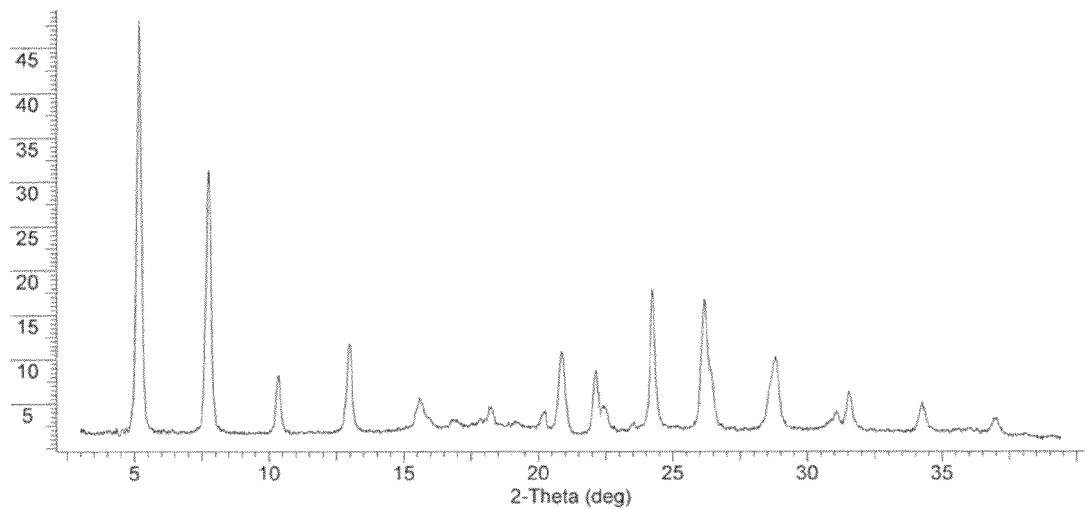

Figure 2.3. X-ray Powder Diffraction Pattern (PXRD) of Modification C
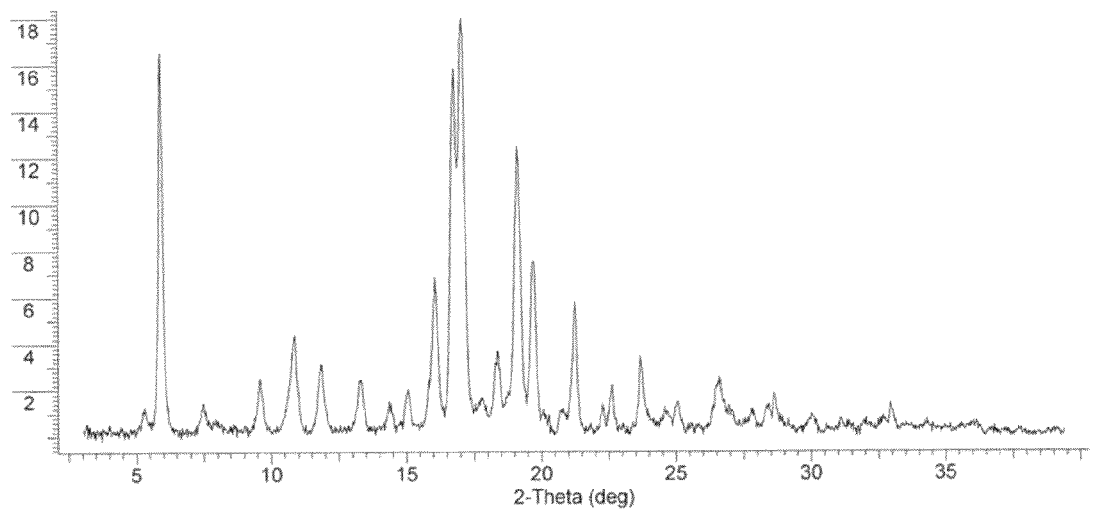
Figure 2.4: X-ray Powder Diffraction Pattern (PXRD) of Modification D
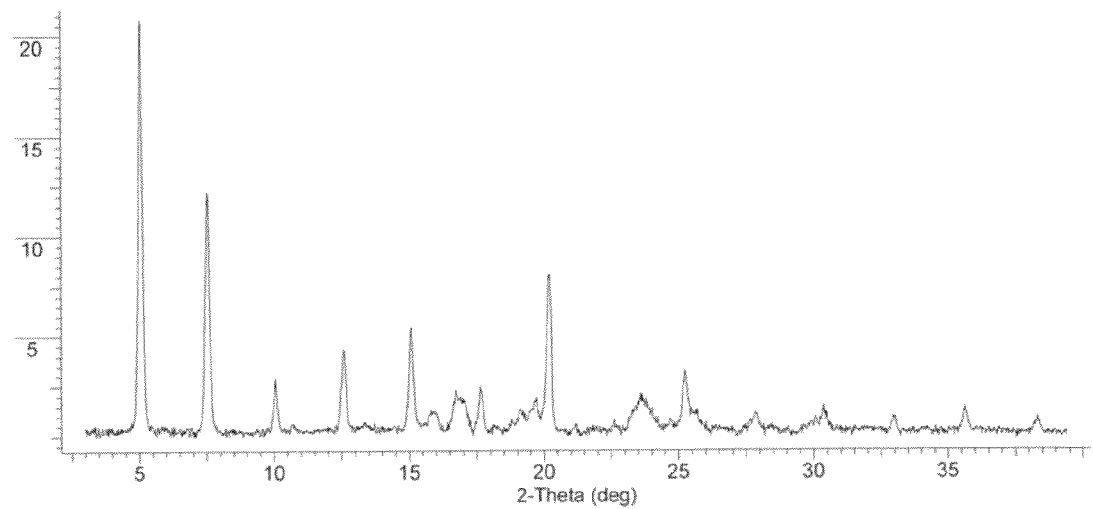

Figure 2.5 X-ray Powder Diffraction Pattern (PXRD) of Modification E
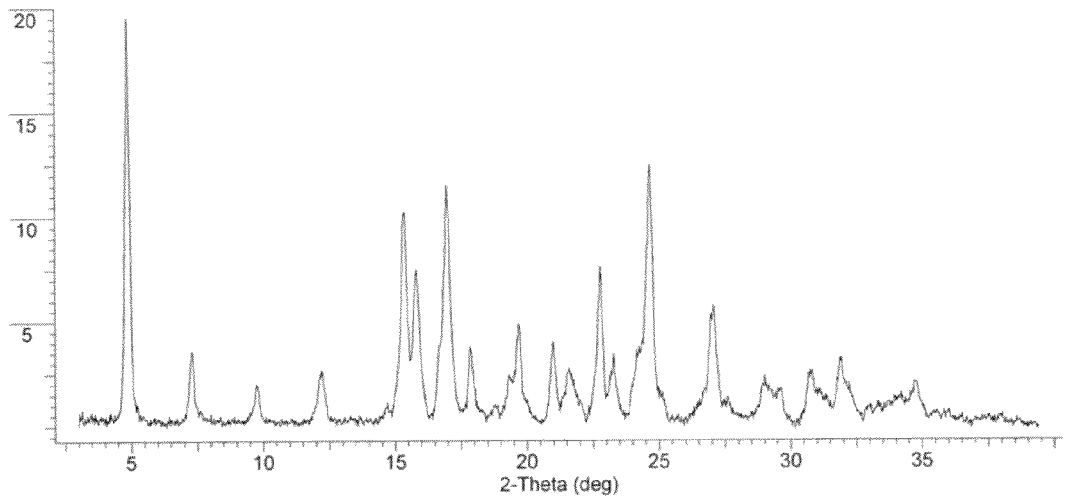
Figure 2.6. X-ray Powder Diffraction Pattern (PXRD) of Modification F
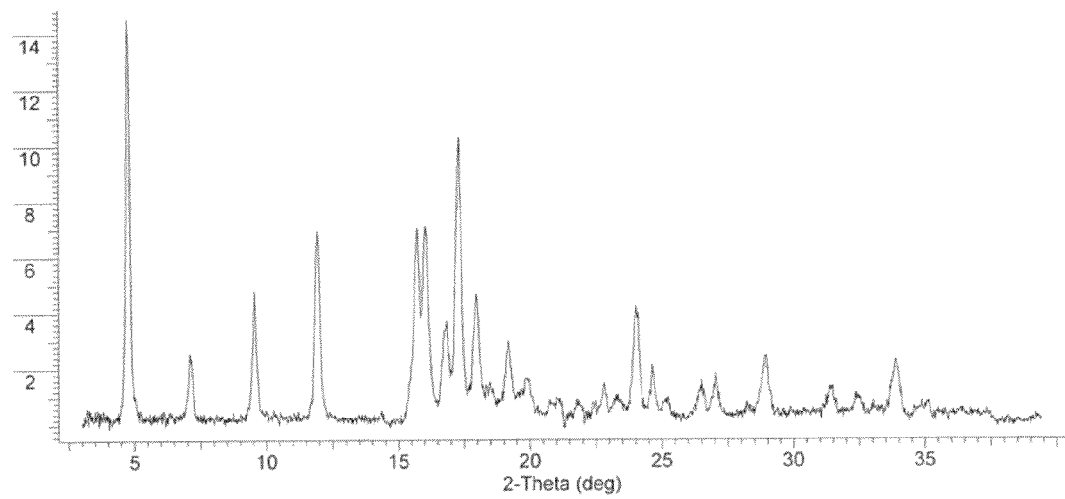

Figure 2.7: X-ray Powder Diffraction Pattern (PXRD) of Modification G
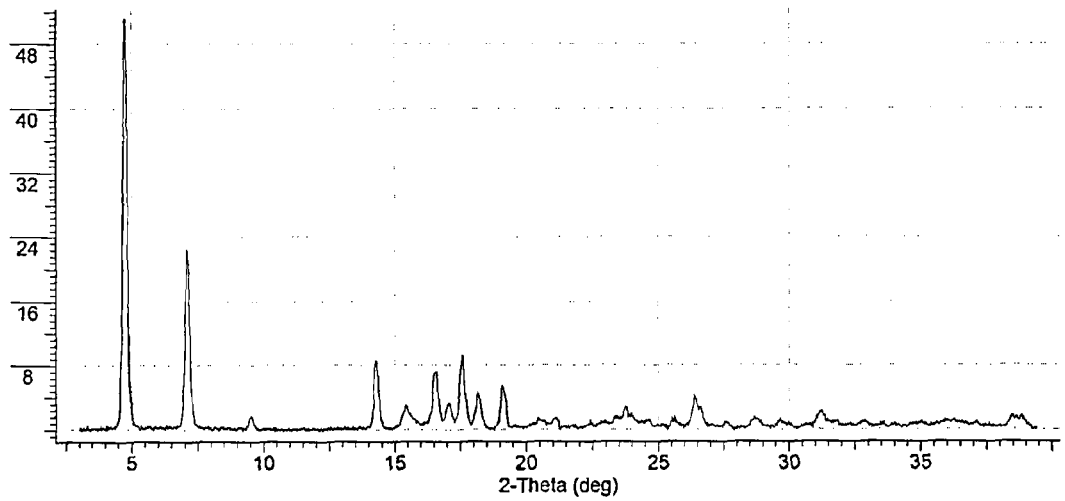
Figure 2.8: X-ray Powder Diffraction Pattern (PXRD) of Modification H
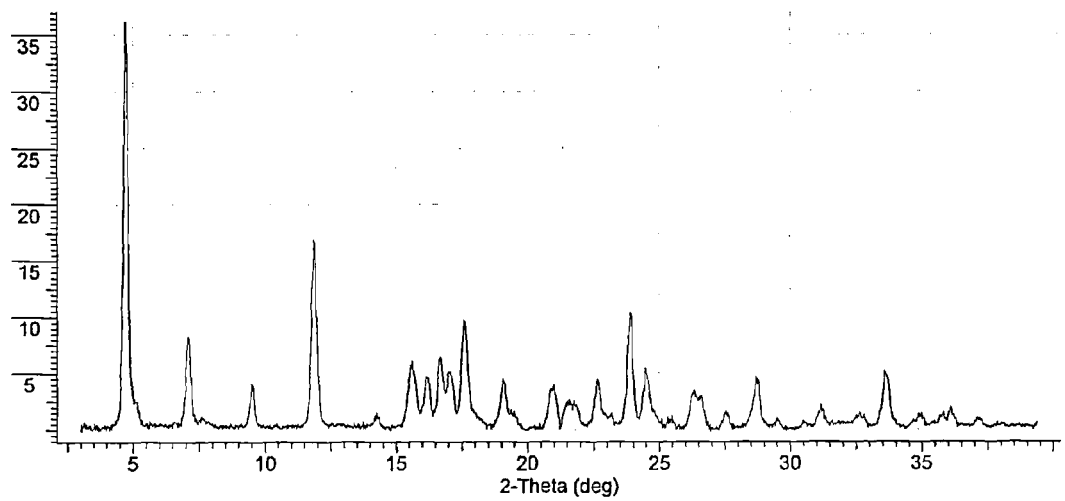

Figure 2.9: X-ray Powder Diffraction Pattern (PXRD) of Modification I
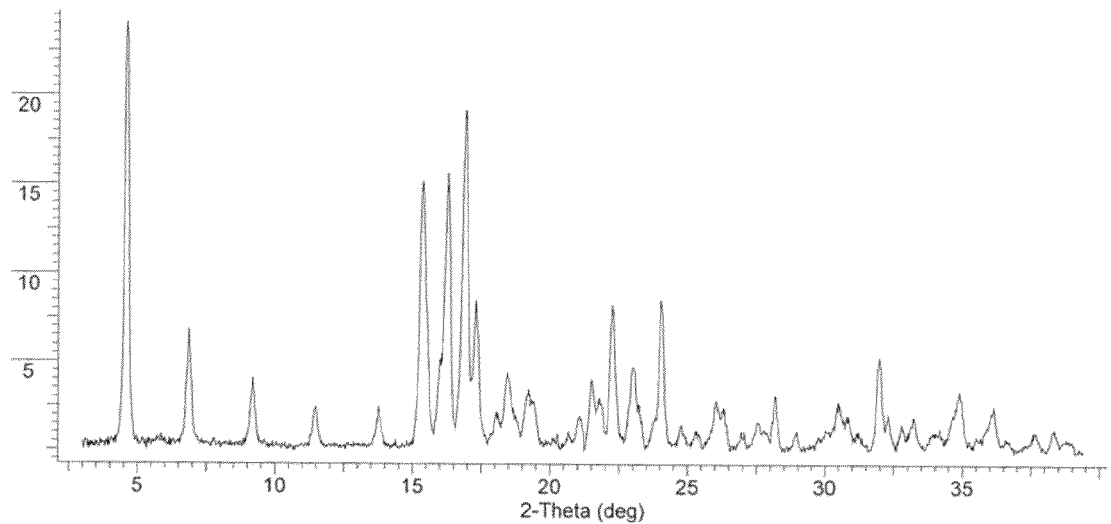
Figure 2.10: X-ray Powder Diffraction Pattern (PXRD) of Modification J
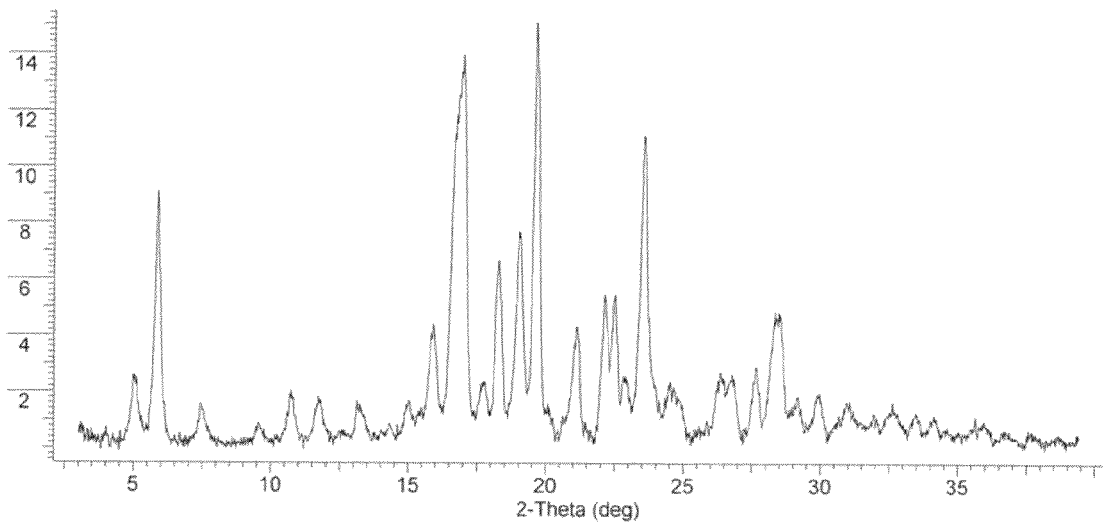

Figure 2.11: X-ray Powder Diffraction Pattern (PXRD) of Modification K
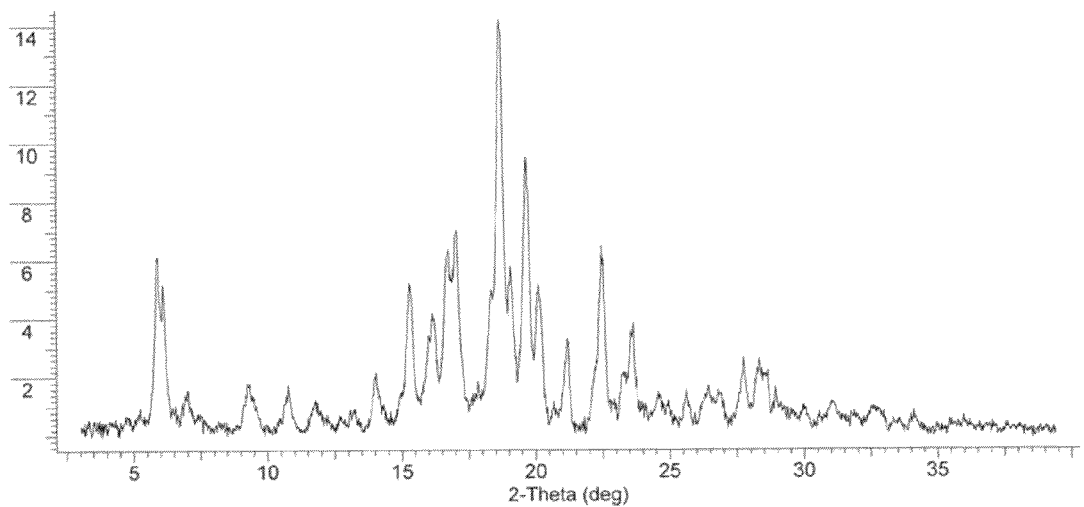
Figure 2.12: X-ray Powder Diffraction Pattern (PXRD) of Modification L
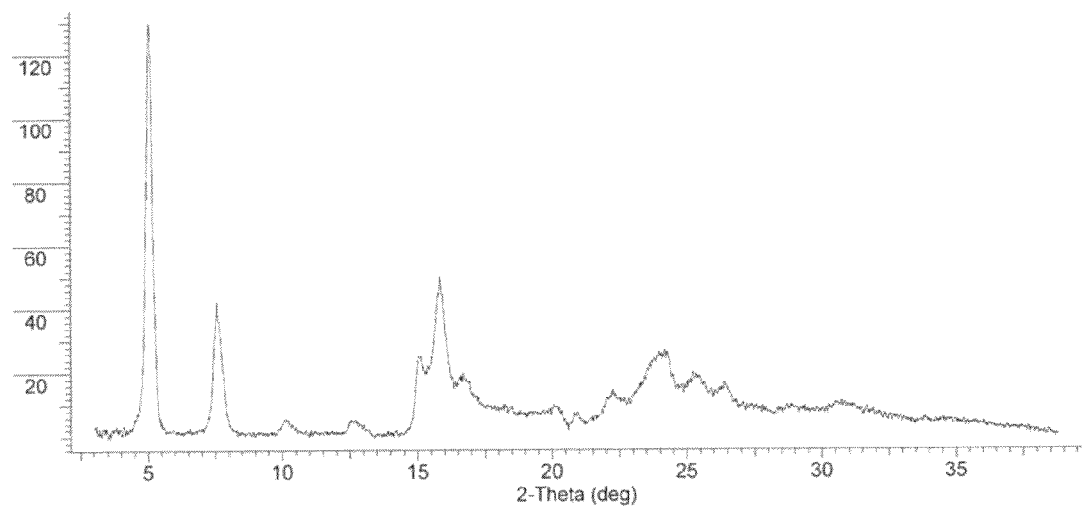

Figure 2.13 X-ray Powder Diffraction Pattern (PXRD) of Modification M
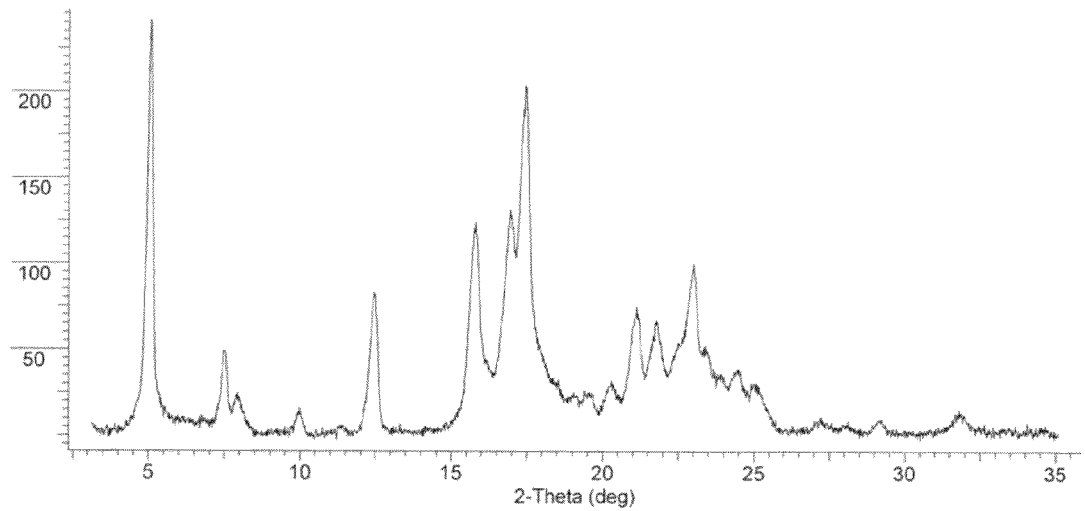
Figure 2.14 X-ray Powder Diffraction Pattern (PXRD) of Modification N
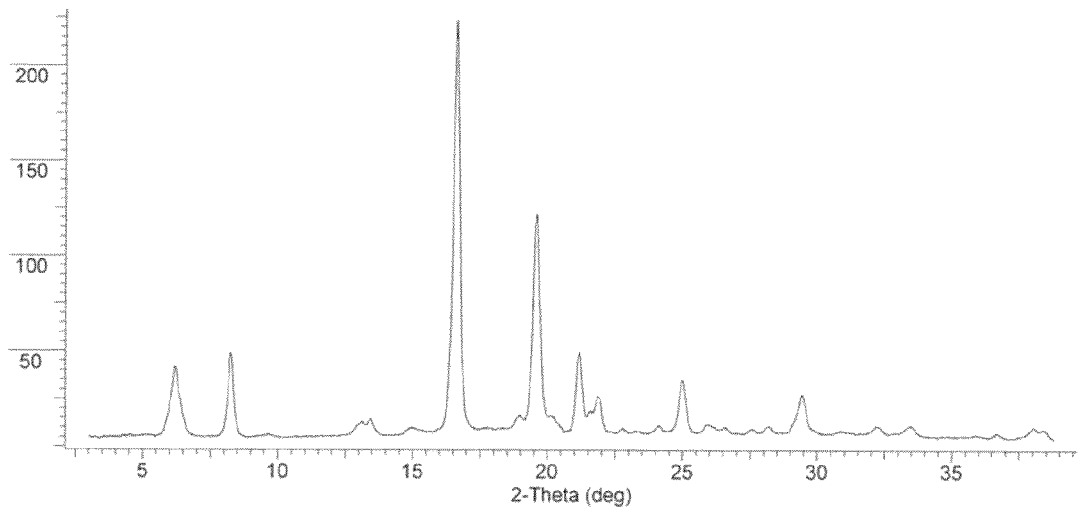

Figure 2.15. X-ray Powder Diffraction Pattern (PXRD) of Modification O
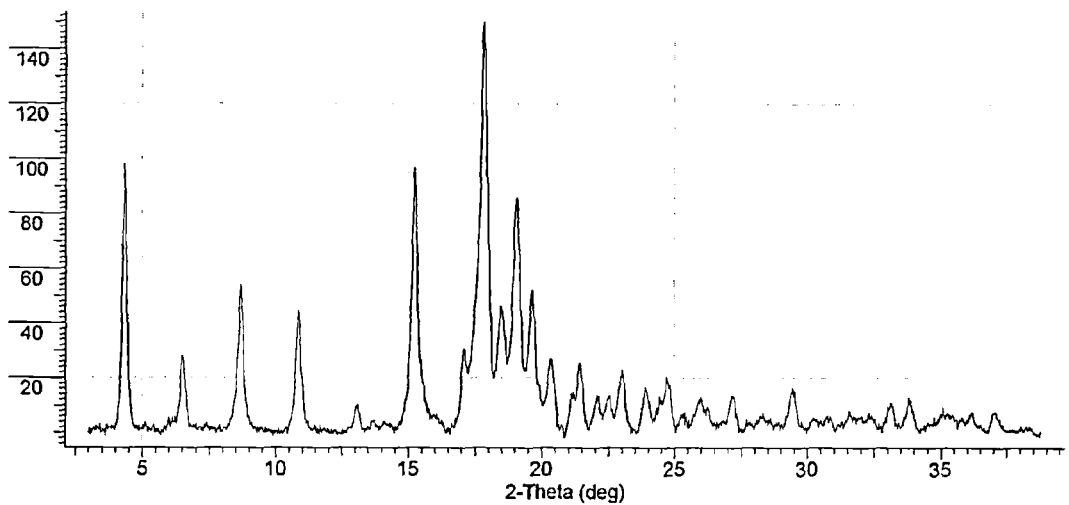
Figure 2.16 X-ray Powder Diffraction Pattern (PXRD) of Modification P
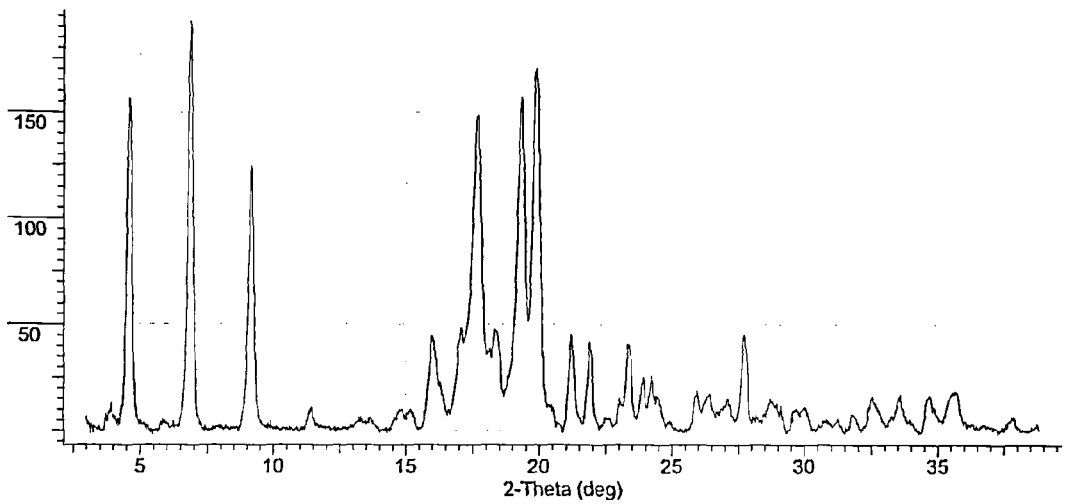

Vacuum thermogravimetric analysis (VTGA) experiment showing the effect of RH (relative humidity) on sample mass of Modification A (20 mbar, 50°C, 32% RH throughout run).

Figure 4: Vacuum thermogravimetric analysis (VTGA) experiment showing the effect of RH (relative humidity) on sample mass of wet cake of Modification C (in acetonitrile and water 8% wt. at 20°C for ~19 hrs.)
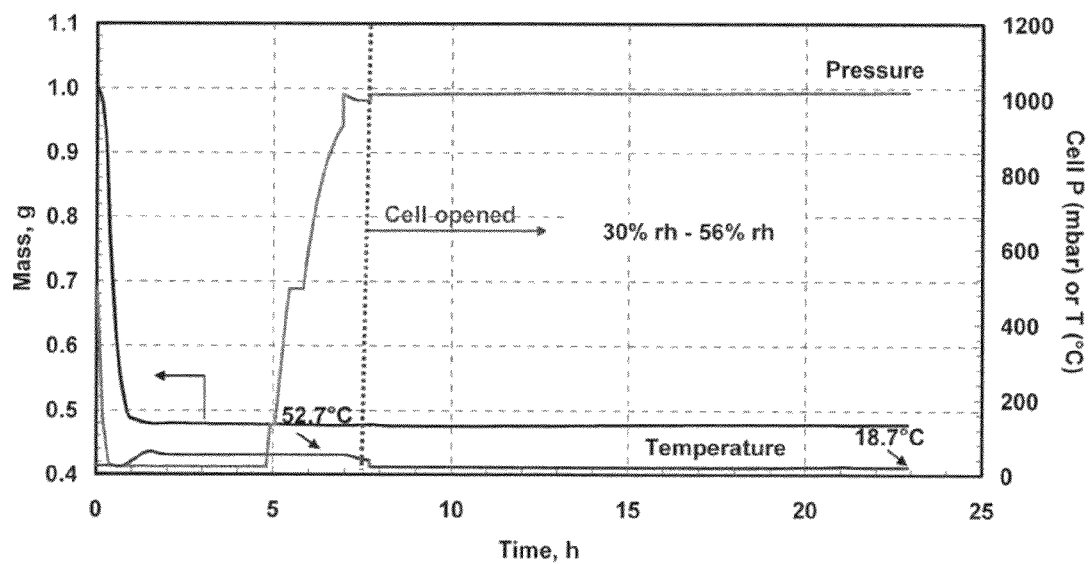

Figure 5    Sorption profile differences at 25°C between Modification A (Form A) and Modification C (Form C)
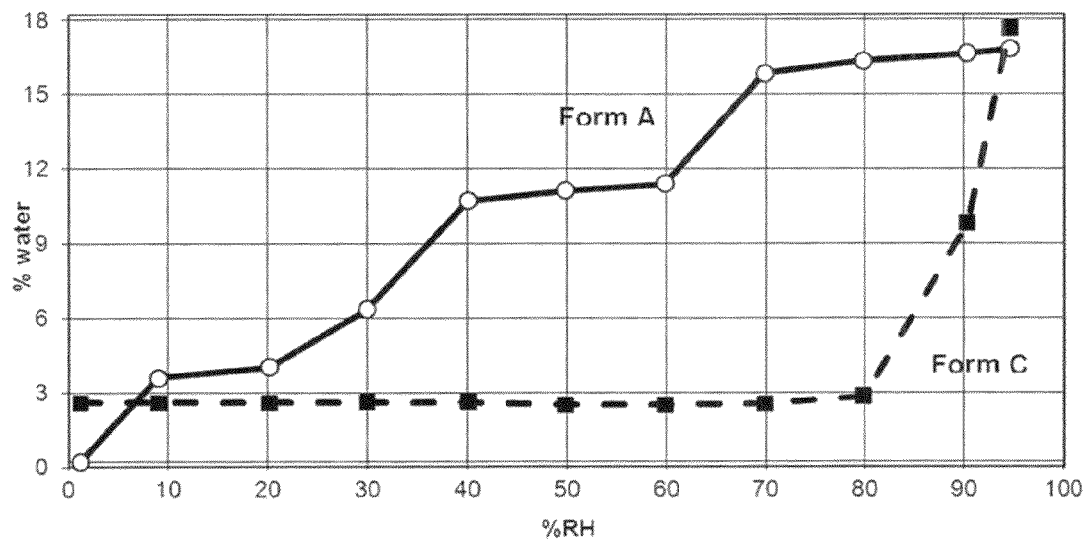
Figure 6    Sorption profile at 25°C of Modification N
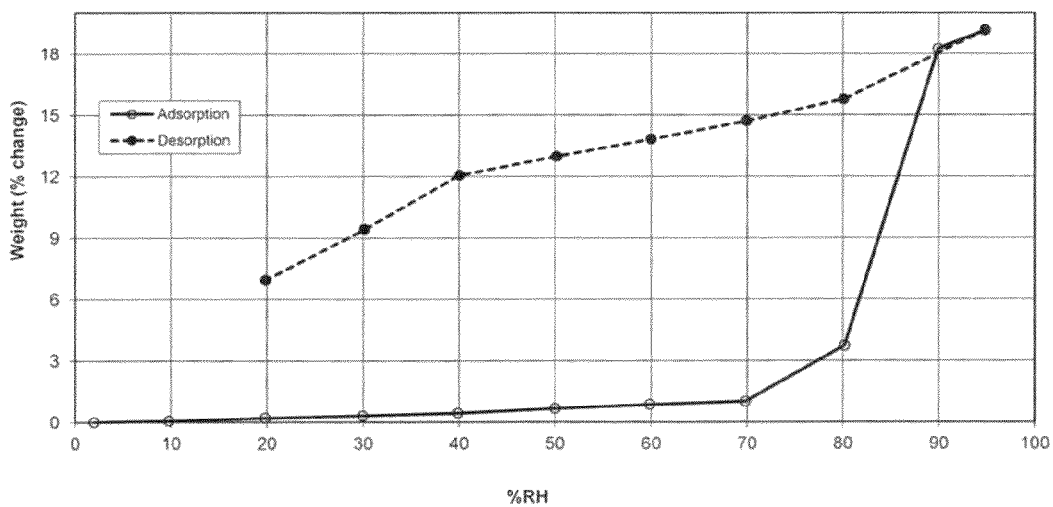

Figure 7   Sorption profile at 25°C of Modification O
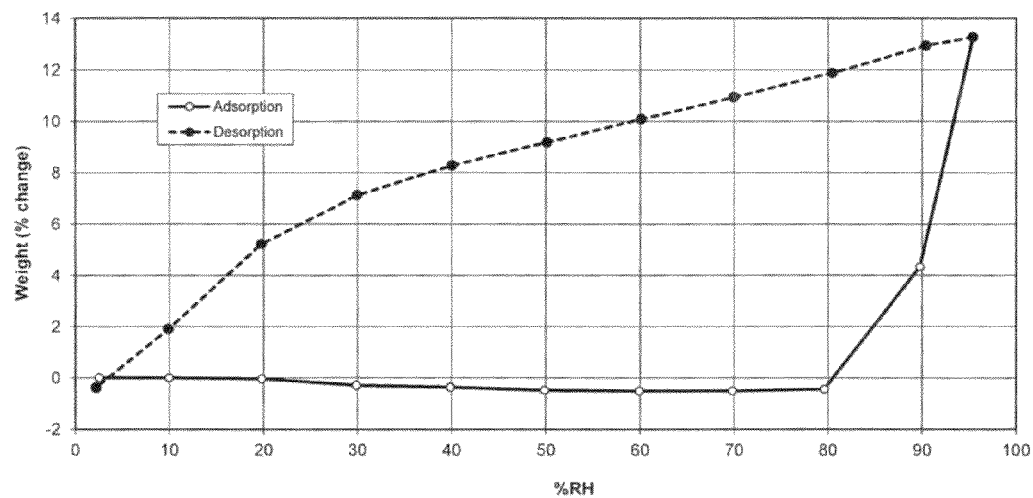
Figure 8   Crystal shapes of Modification A and Modification C
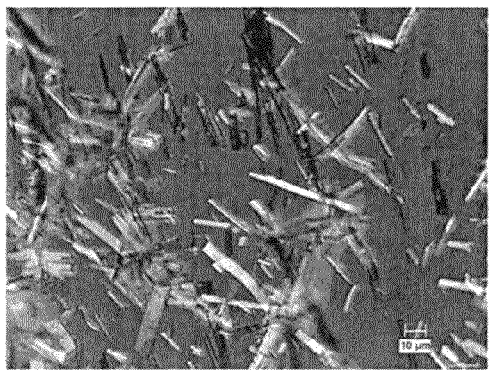
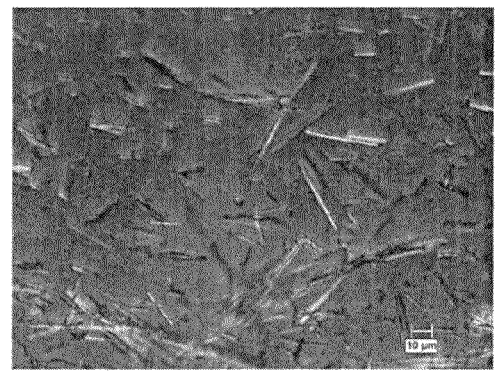
Modification A                    Modification C

CRYSTALLINE FORMS OF THE SODIUM SALT OF (4-{4-[5-(6-TRIFLUOROMETHYL-PYRIDIN-3-YLAMINO)-PYRIDIN-2-YL]-PHENYL}-CYCLOHEXYL)-ACETIC ACID

The present invention relates to novel crystalline forms of the sodium salt of (4-{4-[5-(6-trifluoromethyl-pyridin-3-ylamino)-pyridin-2-yl]-phenyl}-cyclohexyl)-acetic acid and to pharmaceutical compositions comprising these solid forms, and to processes for making such novel forms. The invention further relates to the use of the novel crystalline forms and the compositions thereof, alone or in combination with one or more therapeutic agent, in the treatment of various conditions, particularly in the treatment of a condition or a disorder associated with DGAT1 activity.

WO 2007/126957 describes a genus of compounds which are disclosed to be inhibitors of DGAT1, and therefore useful in the treatment of a condition or a disorder such as inflammatory conditions such as obesity, diabetes and related metabolic disorders. Example 5-1 of said document discloses, the compound (4-{4-[5-(6-trifluoromethyl-pyridin-3-ylamino)-pyridin-2-yl]-phenyl}-cyclohexyl)-acetic acid, having the structural formula (I):

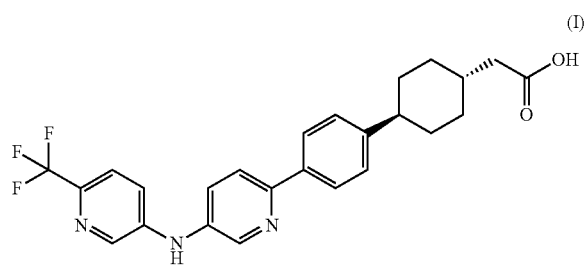 [SMILES: O=C(O)C[C@H]1CC[C@H](c2ccc(-c3ccc(Nc4ccc(C(F)(F)F)nc4)cn3)cc2)CC1]

(I)

and its sodium salt (II)

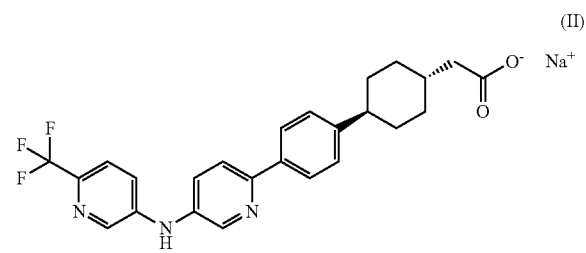

(II)

The procedure described therein for the synthesis of the compound of formula (II) produces a crystalline form which has been subsequently named as 'Modification A' or 'Form A'.

Modification A is hygroscopic, the extent of moisture uptake depending on the ambient relative humidity. Because the ambient humidity impacts the samples' final moisture content, there is batch-to-batch variability in moisture content. The sensitivity of moisture content to ambient humidity can also lead to variability in moisture content between batches produced at different sites and/or at different times of the year. These in turn results in variability in Active Pharmaceutical Ingredient (API) content from batch to batch. In addition to posing quality control problems, these variabilities pose formulation difficulties, as individual batches need to be assayed to quantify the API content. Ideally, a more consistent product that is easier to formulate is required.

In an attempt to produce a more consistent product, controlled re-hydration of the dried crystals of Modification A has been carried out after drying the crystalline form which is obtained after following the procedure described in Example 5-1. Thus, the dried solid is typically exposed to ambient air for at least 48 hours. In a commercial production plant, such a re-hydration step decreases throughput significantly and thus impacts process costs and production times adversely. Additional equipment (e.g., a vessel serving as a source of water vapor for controlled rehydration) is needed, thus increasing processing costs further.

In addition to special requirements for manufacture, the hygroscopic nature of the material also requires that extra care should be taken when analyzing the pharmaceutical formulations for drug substance release.

It is thus important to provide the compound of formula (II) in a physical form which can be reliably prepared and purified on a large scale. That physical form should ideally be stable and not degrade on storage. The physical form chosen must also be stable whilst the drug substance is being manufactured as a formulation which is suitable for the intended route of administration chosen. In that respect, it may be necessary to consider physical properties of the physical form which lead to improved powder handling properties or higher bulk density. In particular, non-hygroscopicity is particularly important in order to obtain good flow characteristics.

The properties of the final product should also be predictable and reliably reproducible. For example, material which is obtained in an inconsistent manner, for example, where the water content differs from batch to batch, must be carefully monitored. This leads to added complications in the handling, manufacture, analysis and formulation of the drug substance.

Whilst one crystalline form may exhibit properties which are considered suitable, another form may also have properties which, with the right measures in place, can lead to its successful development into a drug. The decision as to whether a compound is suitable for commercialization thus depends on finding a crystalline form of the compound which has the right balance of desirable characteristics.

SUMMARY OF THE INVENTION

In one aspect, the present invention provides crystalline forms of the sodium salt of (4-{4-[5-(6-trifluoromethyl-pyridin-3-ylamino)-pyridin-2-yl]-phenyl}-cyclohexyl)-acetic acid

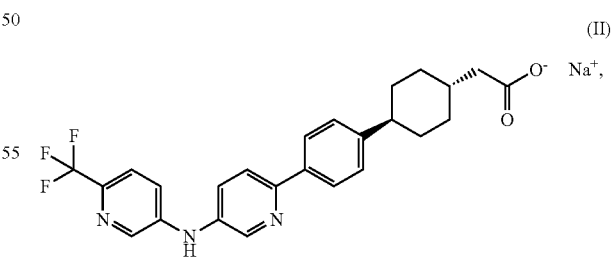

(II)

Embodiments of these crystalline forms include those characterised herein as Modification B, Modification C, Modification D, Modification F, Modification G, Modification H, Modification I, Modification J, Modification L, Modification M, Modification N, and Modification O.

Each crystalline form may be characterised by an X-ray diffraction pattern as set forth in its corresponding Figure.

In another aspect of the invention, there is provided a pharmaceutical composition comprising a crystalline form described herein, and one or more pharmaceutically acceptable carrier or excipient. The composition may comprise at least 90 weight % of the crystalline form of the compound of formula (II), based on the weight of the compound of formula (II) in the composition. In another aspect of the invention, the pharmaceutical composition comprises an additional therapeutic agent.

In a further aspect, there is provided a crystalline form or a pharmaceutical composition as described above, for use in treating or preventing a condition or disorder associated with DGAT1 activity. There is also provided as one aspect of the invention, the use of such a crystalline form or such a pharmaceutical composition for the manufacture of a medicament for treating or preventing a condition or disorder associated with DGAT1 activity.

In a further aspect, there is provided a method for treating or preventing a condition or disorder associated with DGAT1 activity, which method comprises administering to a subject in need thereof a therapeutically effective amount of a crystalline form, or a therapeutically effective amount of the pharmaceutical composition described herein.

In addition, there is provided a process for making any one of the crystalline forms, preferably Modification C.

Further aspects and embodiments of the disclosure are set forth in the following description and claims.

BRIEF DESCRIPTION OF THE FIGURES

FIG. 1 shows the sorption profile of Modification A.

FIG. 2.1 to FIG. 2.16 show the powder X-ray diffraction patterns of Modification A to Modification P respectively.

FIG. 4 shows vacuum thermogravimetric analysis (VTGA) data of Modification C in a drying experiment: drying of Modification C (20 mbar, 50° C.) and subsequent re-exposure to ambient conditions. The trace in black shows the mass of a sample of Modification C.

FIG. 5 shows the difference in hygroscopicity between Modification A and Modification C, as measured by a humidity microbalance. Modification A takes up much more moisture compared to Modification C with increasing humidity.

FIG. 6 shows the sorption profile at 25° C. of Modification N.

FIG. 7 shows the sorption profile at 25° C. of Modification O.

FIG. 8 shows the crystal shapes of Modification A and Modification C. Modification C has smaller crystals than Modification A.

DESCRIPTION

Figure 3:
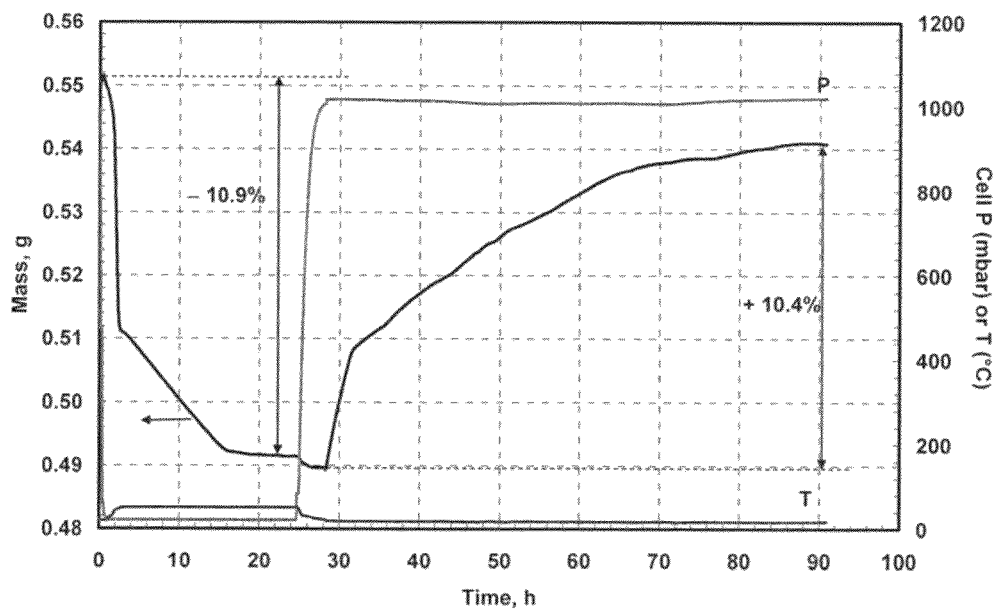
FIG. 3 shows vacuum thermogravimetric analysis (VTGA) data of Modification A in a drying experiment: drying of Modification A (50 mbar, 50° C.) and subsequent re-exposure to ambient conditions. The trace in black shows the mass of a sample of Modification A.

Definitions of various terms which are used herein are listed below.

A particular crystalline form of the compound of formula (II) may be referred to as "crystalline form X", "crystal form X", "polymorph form X", "Modification X", or "H$_X$" where 'X' is the letter which is assigned to that particular crystalline form.

The term "'crystalline form" as used herein include reference to anhydrous crystalline forms, partially crystalline forms, mixture of crystalline forms, hydrate crystalline forms and solvate crystalline forms.

The term "hydrate" as used herein refers to a crystalline form containing one or more water molecules in a three-dimensional periodic arrangement. It can include non-stoichiometric hydrates or stoichiometric hydrates, such as hemihydrates, monohydrates, dihydrates and trihydrates.

The term "solvate" as used herein refers to a crystalline form containing one or more solvent molecules other than water in a three-dimensional periodic arrangement.

The term "compound of the invention" refers to a solid form of the compound of formula (II), preferably Modifications as described in the Examples. It includes anhydrous crystalline forms, partially crystalline forms, mixtures of crystalline forms, hydrate crystalline forms and solvate crystalline forms.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

The present invention includes all crystalline and pharmaceutically acceptable isotopically-labelled forms of the compound of formula (II). In an isotopically-labelled form, one or more atoms are replaced by an atom or atoms having the same atomic number, but an atomic mass or mass number different from the atomic mass or mass number which predominates in nature. Suitable isotopes include isotopes of hydrogen, such as $^2$H and $^3$H; carbon, such as $^{11}$C, $^{13}$C and $^{14}$C; nitrogen, such as $^{13}$N and $^{15}$N; oxygen, such as $^{15}$O, $^{17}$O and $^{18}$O. Certain isotopically-labelled compounds, such as those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds can generally be prepared by conventional techniques known to those skilled in the art or by processes analogous to those described in the accompanying Examples and Preparations using an appropriate isotopically-labeled reagent in place of the non-labeled reagent previously employed.

As used throughout the specification and in the claims, the term "treatment" embraces all the different forms or modes of treatment as known to those of the pertinent art and in particular includes preventive, curative, delay of progression and palliative treatment.

Solid State Physical Properties

Different crystalline or amorphous forms may exhibit different solid state physical properties such as hygroscopicity, behaviour on compaction, stability during storage, and flowability of the milled solid. These properties in turn affect the suitability of a particular solid state form as an active pharmaceutical for commercial production. For example, flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Different crystal forms or amorphous forms of the same drug may also have substantial differences in such pharmaceutically important properties as dissolution rates and bioavailability. Dissolution rates are not only a consideration in formulating syrups, elixirs and other liquid medicaments, they may also have therapeutic consequences. For example, the rate of dissolution of an active ingredient in a patient's stomach fluid can have therapeutic consequences since it imposes an upper limit on the rate at which an orally-administered active ingredient can reach the patient's bloodstream.

These practical physical characteristics are influenced by the conformation and orientation of molecules in the unit cell, which defines a particular polymorphic form of a substance. The polymorphic form may also give rise to thermal behaviour different from that of the amorphous material or another polymorphic form. Thermal behaviour is measured in the laboratory by such techniques as capillary melting point, thermogravimetric analysis (TGA) and differential scanning calorimetry (DSC) and can be used to distinguish some polymorphic forms from others. A particular polymorphic form may also give rise to distinct spectroscopic properties that may be detectable by single-crystal or powder X-ray crystallography, solid state $^{13}$C NMR and $^{19}$F NMR spectrometry and infrared spectrometry. Methods used to characterize the crystal form also include infrared spectroscopy and melting point determination.

Crystalline Forms of the Compound of Formula (II)

The present invention provides a crystalline form of the compound of formula (II), preferably a crystalline form selected from the various modifications detailed herein, preferably Modifications B, C, D, F, G, H, I, L, M, N, and O.

In one embodiment, the crystalline form is selected from Modification B, C, D, F, I, L, N, and O. In another embodiment, the crystalline form is an anhydrous form. In another embodiment, the crystalline form is Modification N or Modification O.

Each modification is characterised by its X-ray diffraction pattern with peaks as essentially depicted in the Figures. Thus, there is provided a crystalline form selected from the various modifications detailed herein, characterized in that said form has an X-ray powder diffraction pattern substantially in accordance with that shown in the corresponding Figure. For instance, there is provided a crystalline form of the sodium salt of (4-{4-[5-(6-trifluoromethyl-pyridin-3-ylamino)-pyridin-2-yl]-phenyl}-cyclohexyl)-acetic acid

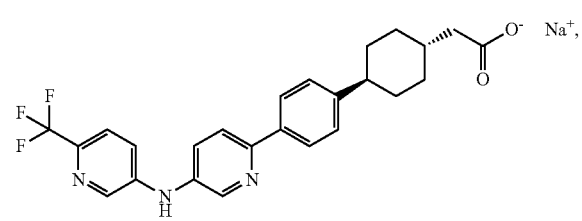

in the form of Modification C, characterized by a powder x-ray diffraction pattern substantially in accordance with that shown in FIG. 2.3;

Alternatively, each modification is characterised by an X-ray diffraction pattern with characteristic peaks as set forth in its corresponding Table. In further embodiments, the present invention provides any of the crystalline forms of the compound of formula (II) as described herein, wherein the angle variation is +/−0.3° 2-theta, or +/−0.2° 2-theta or +/−0.15° 2-theta.

In further embodiments, the present invention provides any of the crystalline forms of the compound of formula (II), as described in the Examples, wherein the crystalline form is characterized by a powder diffraction pattern comprising four or more 2θ values (±0.1 degree) (CuKα λ=1.5418 Å) selected from a group consisting of seven 2θ values as set out under each Example, at a temperature of about 22° C.

For instance, there is provided a crystalline form of the sodium salt of (4-{4-[5-(6-trifluoromethyl-pyridin-3-ylamino)-pyridin-2-yl]-phenyl}-cyclohexyl)-acetic acid

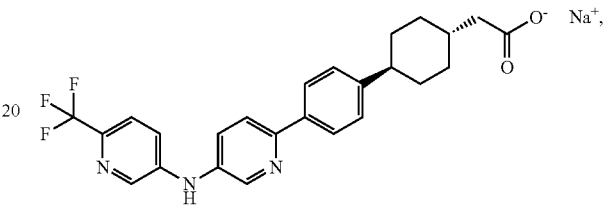

in the form of Modification C, characterized by a powder x-ray diffraction pattern comprising four or more 2θ values (±0.1 degree) (CuKα λ=1.5418 Å) selected from the group consisting of 5.9, 17.0, 19.6, 22.5, 23.6, 28.4 and 30.0, at a temperature of about 22° C.

For instance, there is provided a crystalline form of the sodium salt of (4-{4-[5-(6-trifluoromethyl-pyridin-3-ylamino)-pyridin-2-yl]-phenyl}-cyclohexyl)-acetic acid

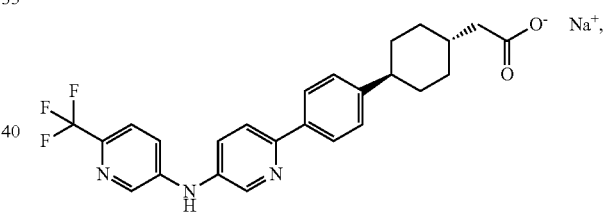

in the form of Modification C, further characterized by a powder x-ray diffraction pattern comprising five or more 2θ values (±0.1 degree) (CuKα λ=1.5418 Å) selected from the group consisting of 5.9, 17.0, 19.6, 22.5, 23.6, 28.4 and 30.0, at a temperature of about 22° C.

In further embodiments, the present invention provides any of the crystalline forms of the compound of formula (II), as described in the Examples, wherein the crystalline form is further characterized by a powder diffraction pattern comprising five or more 2θ values (±0.1 degree) (CuKα λ=1.5418 Å) selected from a group consisting of seven 2θ values as set out under each Example, at a temperature of about 22° C.

In further embodiments, the present invention provides any of the crystalline forms of the compound of formula (II), as described in the Examples, in the form of a specific Modification, characterized in that said form has at least one of the following characteristics:

(a) comprising four or more 2θ values (±0.1 degree) (CuKα λ=1.5418 Å) selected from a group consisting of seven 2θ values (±0.1 degree), at a temperature of about 22° C., as set out for each Modification, or an X-ray powder diffraction pattern substantially in accordance with that shown in the Figure associated with that particular Modification;
(b) a solid state $^{19}$F NMR spectrum comprising peak(s), as set out for each Modification in the Examples section;
(c) a melting point, as set out for each Modification in the Examples section,
(d) a differential scanning calorimetry thermogram, as set out for each Modification in the Examples section.

Thus, for instance, there is provided a crystalline form of the sodium salt of (4-{4-[5-(6-trifluoromethyl-pyridin-3-ylamino)-pyridin-2-yl]-phenyl}-cyclohexyl)-acetic acid

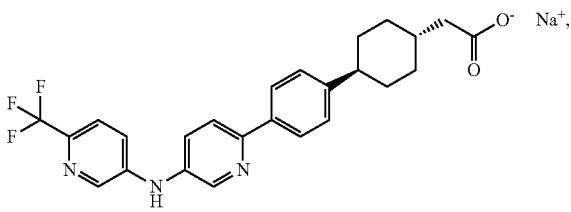

in the form of Modification C,
characterized in that said form has at least one of the following characteristics:
(a) comprising four or more 2θ values (±0.1 degree) (CuKα λ=1.5418 Å) selected from the group consisting of 5.9, 17.0, 19.6, 22.5, 23.6, 28.4 and 30.0, at a temperature of about 22° C., or an X-ray powder diffraction pattern substantially in accordance with that shown in FIG. 2.1;
(b) a solid state $^{19}$F NMR spectrum comprising peaks at −67.6 and −66.0 (±0.2) ppm.;
(c) a melting point with an onset at 246.0° C. (±2.4) and a maximum at 250.1° C. (±2.5);
(d) a differential scanning calorimetry thermogram with an endotherm at 126° C. (±2.5).

In a further aspect of the invention, there is provided consisting essentially of each Modification, or a substantially pure form of each Modification, specially of Modification C. As used herein, "consisting essentially of each Modification" or "substantially pure," when used in reference to a crystalline form, means a compound having a purity greater than 90 weight %, including greater than 90, 91, 92, 93, 94, 95, 96, 97, 98, and 99 weight %, and also including equal to about 100 weight % of the compound of formula (II), based on the weight of the compound. The remaining material comprises other form(s) of the compound, and/or reaction impurities and/or processing impurities arising from its preparation. For example, a crystalline form of the compound of formula (II) may be deemed substantially pure in that it has a purity greater than 90 weight %, as measured by means that are at this time known and generally accepted in the art, where the remaining less than 10 weight % of material comprises other form(s) of the compound of formula (II) and/or reaction impurities and/or processing impurities.

In other embodiments, there is provided a crystalline form comprising at least 80, 85, 90, 95% or 99% by weight of the Modification of interest.

There is also provided a crystalline form comprising at least 95% or 99% by weight of the Modification of interest. Thus, for instance, there is provided a crystalline form comprising at least 95% or 99% by weight of each of the preferred Modifications, especially Modification C, N or O.

In a further aspect, the present invention provides a hydrate, monohydrate, trihydrate, or a semi-hydrate of the compound of formula (II).

In a further aspect, the present invention provides an anhydrous form of the compound of formula (II).

Preparation of Crystalline Forms of the Compound of Formula (II)

In a further aspect, the present invention provides the use of Modification B to produce Modification A.

In a further aspect, the present invention provides the use of Modification A to produce Modification C.

In a further aspect, the present invention provides the use of any of the crystalline forms described herein, to produce another crystalline form. Preferably, Modification A is used to produce another crystalline form, more preferably, to produce Modification C.

The present invention also provides a process for the preparation of Modification C wherein a compound of formula (II), e.g. in the form of Modification A is dispersed or slurried in a solvent system, the resulting slurry filtered and the residue obtained after filtration dried.

Alternatively, the solvent system may be a single solvent system, wherein the solvent includes THF, preferably anhydrous THF, acetone, butanol, ethanol and ethyl acetate.

The organic solvent system may also be a binary solvent system. Preferably, the binary solvent system is a combination of a strong solvent (i.e. a solvent in which the drug substance has a high solubility, e.g. >20 mg/ml, such as dimethyl sulfoxide (DMSO), methanol or ethanol; and a weak solvent (i.e. a solvent in which the drug substance is significantly less soluble, e.g. <1 mg/ml, such as acetonitrile, t-butyl acetate, ethyl acetate, toluene, i-propyl acetate. Preferably the ratio of the strong solvent to the weak solvent is 1:4 to 1:1, more preferably 1:1.

The binary solvent system may be an aqueous binary solvent system, wherein the water content is less than 8 wt %, preferably, 3-6 wt %, of the mass of dry starting material.

The solvent water content is critical for obtaining good conversion; when the solvent water content exceeds 8 wt % of the mass of the compound of formula (II), no conversion to Modification C occurs. Thus, the water content is preferably not more than 8 wt %, more preferably, 3-6 wt % of the mass of dry starting material.

The process may be carried out at room temperature or at higher temperatures, e.g. at 45° C.

In one embodiment of the invention, Modification A particles are dispersed in tetrahydrofuran at 45° C. to prepare Modification C.

In a further embodiment of the invention, Modification A particles are dispersed in acetonitrile/water (8 wt %) at room temperature to prepare Modification C.

Modification C may also be obtained using a process wherein a crystallization from a clear solution is used to prepare Modification C. This has the major advantage that this would comply with requirements imposed by some drug regulatory authorities, e.g. the Food Drug Agency's Good Manufacturing Practices (GMP) requirements, in that a clarifying filtration from a clear solution is carried out in the drug substance production step itself, in order to remove any insoluble particles. In addition, the recrystallization process requires no addition of water and utilizes the water present in the starting material, e.g. Modification A (8-10 wt %), making it inherently robust.

The present invention thus also provides a process for the preparation of Modification C using a recrystallisation method comprising the steps of
(a) dissolving the compound of formula (II) in a solvent system, wherein said solvent system is either dimethyl sulfoxide (DMSO) or a mixture of tetrahydrofuran and ethanol;

(b) adding (i) a solvent which is selected from acetonitrile, toluene and methyl-t-butyl ether; or (ii) a mixture of and water and a solvent which is selected from acetonitrile, toluene and methyl-t-butyl ether, wherein the water content is 0.25 to 3% v/v; or (iii) an anti-solvent such as heptane;
(c) filtering the mixture obtained at the end of step (b);
(d) optionally drying the crystals.

If desired, Modification C seed particles may be added to aid the crystallisation process.

The solubility of Modification A is relatively low in common process solvents. To achieve an acceptable throughput, it is thus important to utilize a solvent system that can dissolve large amounts of Modification A solids. The solvent system may thus be a single organic solvent (e.g., DMSO, or methanol) or a mixture of two organic solvents.

In one embodiment, the organic solvent is a mixture of two organic solvents, more preferably of tetrahydrofuran and ethanol. The ratios of the two organic solvents may vary, but is preferably one which gives superior process throughput and yield, e.g. a 1:1 v/v ratio).

Hence in a preferred embodiment, an equal volumetric ratio of THF/Ethanol is used, preferably at room temperature.

The method may be carried out at room temperature or above. A higher temperature, preferably between 40-50° C., more preferably 45-50° C., is preferred as the level of impurities in the crystals obtained is considerably lower when the drug substance is crystallized from higher temperatures.

An anti-solvent such as t-butyl methyl ether, acetonitrile and heptanes may also be used in this process. Heptanes are preferred as they give a cleaner profile for the resulting solids.

Administration and Pharmaceutical Formulations

The compounds of the invention will normally be administered orally, intravenously, subcutaneously, buccally, rectally, dermally, nasally, tracheally, bronchially, by any parenteral route, as an oral or nasal spray or via inhalation. Parenteral modes of administration include intravenous, intramuscular, intraperitoneal, intrasternal, subcutaneous and intraarticular injections and infusions. Pharmaceutical compositions suitable for the delivery of the compounds of the invention and methods for their preparation may be found, e.g. *Remington's Pharmaceutical Sciences, 19th Edition*, (Mack Publishing Company, 1995).

The compounds of the invention may be administered orally. Advantageously, the compounds of the invention may be orally active, have rapid onset of activity and low toxicity. Oral administration may involve swallowing, so that the compound enters the gastrointestinal tract, or buccal or sublingual administration may be employed by which the compound enters the blood stream directly from the mouth.

Examples of formulations suitable for oral administration are solid formulations such as tablets, capsules containing particulates, liquids, or powders, lozenges (including liquid-filled), chews, multi- and nano-particulates, gels, solid solution, liposome, films, ovules, sprays and liquid formulations.

Examples of liquid formulations include suspensions, solutions, syrups and elixirs. These may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The compounds may be administered alone or as compositions in combination with pharmaceutically acceptable diluents, excipients or carriers. The present invention thus provides a pharmaceutical composition comprising a therapeutically effective amount of a compound of the invention, alone or in combination with one or more pharmaceutically acceptable carriers (excipients).

Examples of such carriers or excipients include:
a) a diluent, e.g., lactose, dextrose, sucrose, mannitol, sorbitol, cellulose and/or glycine;
b) a lubricant, e.g., silica, talcum, stearic acid, its magnesium or calcium salt and/or polyethyleneglycol;
c) a binder, e.g. magnesium aluminum silicate, starch paste, gelatin, tragacanth, methylcellulose, sodium carboxymethylcellulose and or polyvinylpyrrolidone;
d) a disintegrant, e.g., starches, agar, alginic acid or its sodium salt, or effervescent mixtures; and/or
e) an absorbant, a colorant, a flavor and/or a sweetener.

Additional examples of useful excipients are described in the Handbook of pharmaceutical excipients, 3rd edition, Edited by A. HOURS. Kibbe, Published by: American Pharmaceutical Association, Washington D.C., ISBN: 0-917330-96-X, or Handbook of Pharmaceutical Excipients (4th edition), Edited by Raymond C Rowe—Publisher: Science and Practice which are incorporated herewith by reference.

Depending upon the disorder and patient to be treated and the route of administration, the compositions may be administered at varying doses. In general, the daily dose range of the compound of the invention lies within the range of from about 0.0001 mg/kg to about 100 mg/kg, preferably from about 0.001 mg/kg to about 50 mg/kg body weight of a subject in single or divided doses. On the other hand, it may be necessary to use dosages outside these limits in some cases.

In the case where an oral composition is employed, a suitable dosage range of the compound of the invention is, e.g. from about 0.001 mg/kg to about 100 mg/kg body weight of a subject in the composition per day, preferably from about 0.01 mg to about 2000 mg per day. For oral administration, the compositions are preferably provided in the form of tablets containing from 0.01 mg to 2,000 mg, e.g. 0.01, 0.05, 0.1, 0.2, 0.5, 1.0, 2.5, 5, 10, 15, 20, 25, 30, 40, 50, 75, 80 milligrams.

In one embodiment, the compound of the invention is used at a dose of 5-40 mg, of 10-40 mg, or of 20-40 mg. In another embodiment, the DGAT1 inhibitor is used at a dose of 5, 10, 15, 20, 25, 30 or 40 mg. In a preferred embodiment, the DGAT1 inhibitor is used at a dose of 5, 10, or 20 mg, based on the amount of the compound of formula (I).

It is to be understood that the doses quoted herein refer to the DGAT1-inhibitor itself. When a pharmaceutically acceptable salt of the DGAT1-inhibitor is used, the doses used will need to be adjusted accordingly.

The present invention further provides a pharmaceutical composition, preferably a tablet or a gelatine capsule, as herein described, comprising a second active ingredient (i.e. combination partner) as described below in the 'Combination therapy' section.

Accordingly, the present invention provides a pharmaceutical composition as described herein as for use as a medicament. A pharmaceutical composition as described herein is also provided for use in the treatment of a disorder or a condition associated with DGAT1 activity. A pharmaceutical composition as described therein for the manufacture of a medicament for the treatment of a disorder or a condition associated with DGAT1 activity is also provided.

A method of preventing or treating a disorder or a condition associated with DGAT1 activity comprising administrating a therapeutically effective amount of the composition to a subject in need of such a treatment is also provided.

Use

As described herein above, the compounds of the present invention may be useful for the treatment or prevention of a disorder or a condition mediated by DGAT1 activity in animals, particularly humans.

Thus the present invention also provides a method for treating or preventing a condition or a disorder associated with DGAT1 activity, which method comprises administering a therapeutically effective amount of the compound of the invention to a subject in need thereof.

Thus the present invention provides the use of a compound of the invention, alone or in combination with another therapeutic agent (see below) for the manufacture of a medicament for treating or preventing a conditions or a disorder associated with DGAT1 activity in animals, particularly humans. A compound of the invention, alone or in combination with another therapeutic agent (see below) is also provided for use in treating or preventing a condition or a disorder associated with DGAT1 activity in animals, particularly humans.

Conditions or disorders associated with DGAT1 activity include metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, chylomicronemia, familial chylomicronemia syndrome, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris. In yet another aspect, the present invention provides methods of using a compound or composition of the invention as an anorectic.

More preferably, the condition or disorder associated with DGAT1 activity is impaired glucose tolerance, Type 2 diabetes and obesity, chylomicronemia, or familial chylomicronemia syndrome.

Combination Therapies

The treatment of prevention of the DGAT1-related a disorder or a condition listed above consists of administering to a subject in need thereof a therapeutically effective amount of a compound described in this invention. The treatment may also include the administration of a therapeutically effective amount of a compound of the invention and a therapeutically effective amount of at least one further pharmaceutically active compound. Accordingly, the invention provides a pharmaceutical composition comprising a compound of the invention and at least one additional therapeutic agent. The combination may also be administered simultaneously or sequentially in any order, separately or in a fixed combination (e.g. in the same pharmaceutical composition).

In particular, a composition or product of the invention may further comprise a therapeutic agent selected from a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;

b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid bile acid binding resins such as cholestyramine; fibrates; nicotinic acid and other GPR109 agonists; cholesterol absorption inhibitors such as ezetimibe; CETP inhibitors (cholesterol-ester-transfer-protein inhibitors), and aspirin;

c) anti-obesity agents such as orlistat, sibutramine and Cannabinoid Receptor 1 (CB1) antagonists e.g. rimonabant; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors: ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e.

compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

In each case in particular in the compound claims and the final products of the working examples, the subject matter of the final products, the pharmaceutical preparations and the claims are hereby incorporated into the present application by reference to these publications and patent applications.

The weight ratio of the compound of the present invention to the further active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. The herein described daily dosages are conveniently administered once (once a day administration) or in divided dosages (e.g. divided for a twice daily administration).

The present invention also relates to the use of a combination as hereinabove described for the manufacture of a medicament for treating or preventing a condition or a disorder associated with DGAT1 activity in animals, particularly humans. A combination as herein above described for use in the treatment or prevention of a condition or disorder associated with DGAT1 activity in animals, particularly humans, is also provided.

The present invention also provides a method for treating or preventing a condition or a disorder associated with DGAT1 activity, which method comprises administering daily to a subject in need thereof a combination as hereinabove described.

Likewise, the present invention provides a method as defined above comprising co-administration, e.g., concomitantly or in sequence, of a therapeutically effective amount of a compound as defined in the claims and described above, or a pharmaceutically acceptable salt thereof, and a second drug substance, said second drug substance being an anti-diabetic, a hypolipidemic agent, an anti-obesity agent or an anti-hypertensive agent, e.g., as indicated above.

EXAMPLES

The following abbreviations are used herein.

| | |
|---|---|
| L | Litre |
| LOD | Loss on drying |
| mL | millilitre |
| r.h. or RH | Relative humidity |
| TG/DTA | Thermogravimetric/Differential Thermal Analysis |
| THF | Tetrahydrofuran |
| VTGA | Vacuum thermogravimetric analysis |

Other abbreviations used are those conventional in the art.
Methodology, Instruments and Standards Used
(i) Powder X-Ray Diffraction (PXRD)

The powder X-ray diffraction pattern was determined using an Instrument Bruker D8 discovery diffractometer.

The X-ray diffraction pattern was recorded between 2° and 35° (2 theta) with Cu K radiation (45 kV, 40 mA). The measurements were performed at about 45 kV and 40 mA under the following conditions:
Scan rate: 0.5° (2 theta)/min
Chopper increment: 0.02°
Slits (from left to right): 2, 3, 0.3, 0.2 mm PXRD-Method
Instrument Bruker D8 discovery
IrradiationCuK (40 kV, 40 mA)
$CuK_1$=1.540598 Å
Scan range 3°-40° (2 theta value)
Scan type: 2theta scan/detector scan (HI-STAR detector)
Step time 180 seconds
Step size 0.02 deg
Temperature 20° C. to 25° C.

PXRD profiles for the respective solid forms are shown in the Figures.

List of characteristic peaks are listed herein in the Tables below and described in the Figures. The peaks listed herein are given in degrees two theta (±0.1 degree).

As will be appreciated by the skilled person, the relative intensities of the various peaks within the Tables given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Tables. The skilled person will also appreciate that measurements using a different wavelength will result in different shifts according to the Bragg equation—$n\lambda=2d \sin \theta$. Such alternative PXRD patterns generated by use of alternative wavelengths are nevertheless representations of the same material.

(ii) Thermogravimetric/Differential Thermal Analysis (TG/DTA)

Differential scanning calorimetry was conducted for each crystalline form using a TA Instruments™ model Q1000. For each analysis, the DSC cell/sample chamber was purged with 100 ml/min of ultra-high purity nitrogen gas. The instrument was calibrated with high purity indium. The heating rate was 10° C. per minute in the temperature range between 25 and 300° C. The heat flow, which was normalized by sample weight, was plotted versus the measured sample temperature. The data were reported in units of watts/gram ("W/g"). The plot was made with the endothermic peaks pointing down. The endothermic melt peak (melting point) was evaluated for extrapolated onset temperature.

| TG/DTA-method | |
|---|---|
| Instrument | Seiko TG/DTA |
| Temperature range | rt-295° C. |
| Scan rate | 10°/min |
| Nitrogen flow | 100 ml/min |

As used herein, the terms "a concentration of a given modification in a given solvent (X), another solvent (Y) is added" means the solution obtained after the given modification is dissolved in the former solvent (X) to a high concentration (>75 mg/ml) and the latter solvent (Y) is added to initiate crystallization.

(iii) $^{19}$F Solid State NMR $^{19}$F solid state NMR was run on a 500 MHz Bruker NMR Spectrometer with the following parameters:
HFX 4 mm "MAS" Probe;
$^{19}$F frequency is 470.55 MHz;
$^1$H high power ("spinal64" sequence for rigid solids) decoupled $^{19}$F NMR;
Magic Angle Spinning speed: 10 KHz; 4 mm MAS rotor;
Number of scans 4.

Reference used is trichlorofluoromethane (CCl$_3$F). The fluorine signal is 0.0 ppm. The peaks listed for $^{19}$F solid state NMR spectra are given in ppm (±0.2 ppm).

Reference Example 1

Modification A (Also Referred to as Form A)

Modification A may be prepared according to the procedure described in Example 5-1 of WO 2007/126957.

Alternative Procedure for Preparing Modification A (Also Referred to as Form A)

Alternatively, Modification A may be prepared according to the following procedure.

A 2-L flask is charged with 42.83 g of (4-{4-[5-(6-trifluoromethyl-pyridin-3-ylamino)-pyridin-2-yl]-phenyl}-cyclohexyl)-acetic acid, sodium salt, (as obtained in Example 5-1 of WO 2007/126957), 1246 mL of ethyl acetate, and 38.5 mL of water. The suspension is heated to 40° C. and stirred at 40±2° C. for 8 hours. The suspension is filtered and the cake washed with 300 mL of ethyl acetate. The cake is collected and dried at 50° C. under vacuum for 16 hours until LOD <0.5%. After removing from the vacuum dryer, the powder is exposed to ambient conditions for several hours to allow hydration. 40.53 g of Modification A are obtained as a hygroscopic off-white to white solid.

When characterized by powder X-ray diffraction, Modification A gives the pattern shown in FIG. 2.1. The characteristic peaks (±0.1 degree) are given in the Table below.

TABLE

X-ray diffraction pattern for sodium salt crystalline form A (Modification A)

| No. | Angle 2θ (degrees) (±0.1 degree) | Relative Intensity (%)I |
|---|---|---|
| 1 | 5.1 | 57.7 |
| 2 | 7.7 | 32.7 |
| 3 | 10.2 | 7.1 |
| 4 | 12.8 | 4.8 |
| 5 | 15.4 | 12.3 |
| 6 | 16.2 | 5.8 |
| 7 | 16.7 | 6.1 |
| 8 | 17.2 | 13.9 |
| 9 | 17.8 | 15.5 |
| 10 | 18.6 | 7.5 |
| 11 | 20.5 | 7.5 |
| 12 | 22.4 | 7.4 |
| 13 | 22.8 | 3.6 |
| 14 | 23.7 | 3.1 |
| 15 | 24.5 | 11.0 |
| 16 | 25.7 | 8.1 |
| 17 | 26.8 | 7.7 |
| 18 | 28.9 | 7.1 |
| 19 | 30.1 | 3.3 |
| 20 | 31.2 | 5.2 |

The x-ray diffraction changes with hydration level with Modification A. The above x-ray pattern is obtained under ambient conditions, i.e. at a temperature between 20° C. and 25° C., and a relative humidity between 40% and 65%.

DSC data showing the melting transitions of Modification A are displayed below. The melting point and peak area of a compound are often indicative of relative physical stability between different crystalline forms.

| Form | Onset/° C. ± 2.4 | Maximum ° C. ± 2.5 | Area (ΔH) mJ/mg |
|---|---|---|---|
| A | 259.4° C. | 264.0° C. | 19.3 |

The data listed below show the total water loss (LOD by thermogravimetry (TG)) and thermal transitions (DTA signals) show the temperature at which the water is lost. Modification A shows two endotherms at 41° C. to 67° C. that are indicative of this crystalline form.

TABLE

Water loss as a function of temperature as measured by TG/DTA

| Form | Loss On Drying (LOD) (%) | LOD (thermal transitions) |
|---|---|---|
| A | 9.1 | 41° C., 67° C. |

Properties of Modification A

Modification A is obtained as a crystalline hydrate which may contain 0% to 17%, moisture. The absorption-desorption isotherms of form A is plotted in FIG. 1. Each plateau defines a separate crystal form defined by distinctively different x-ray diffraction powder patterns. The plateau at about 12% weight change (form A) shows the relative humidity range for which modification A is stable. Form A is stable over a humidity range ranging from 30% to 60% relative humidity, so this form would exist under most ambient conditions. Typically, it is found to contain a water level of approximately 8%-12%.

Modification A is very hygroscopic. The extent of moisture uptake depends on the ambient relative humidity, with more uptake occurring at higher ambient relative humidity (FIG. 1-*solid* line). FIG. 1 (dotted line) also shows that mass loss due to desorption of water after rehydration can also occur as relative humidity decreases.

Physical Stability

Modification A converts to another form in samples that have not been refrigerated. Modification A shows a reversible powder diffraction pattern change over the short term and an irreversible change over the long run.

Modification M is produced by complete dehydration of modification A. FIG. 1 shows that modification M is only stable below 10% relative humidity. Form H is stable only between 10% and 30% relative humidity and form G is stable in the relative humidity range of 60% to 90%.

Vacuum Thermogravimetric Analysis (VTGA) of Modification A

The wet solid obtained by filtering the crystallization slurry is placed in a cup placed in a cell (i.e., a small chamber) and suspended form a microbalance; vacuum is applied to the cell, and the chamber is subsequently heated. The sample mass is monitored and recorded continuously, indicating when the sample drying is complete and if moisture uptake occurs when the cell is opened to the ambient atmosphere. FIG. 3 shows the drying of Modification A in a VTGA experiment. After applying vacuum (giving 50 mbar of absolute pressure) and heating the sample in the chamber to 50° C., the sample mass decreases to a steady value after about 18 hours, indicating that drying is complete; upon opening the cell (pressure=1000 mbar, temperature drops to ambient value), the sample mass increases steadily due to moisture uptake, finally reaching a plateau at ca. 90 hours (total mass gain at that point being 10.4%). This shows that Modification A is highly hygroscopic. This also shows that the process for making modification A is more dependent of the ambient humidity than, say, for modification C (see below).

The VTGA data also show that modification A takes several hours to dry and must be rehydrated to generate the target modification. The rehydration step may take several days on a production scale. In contrast, drying modification C (see below) takes 10% of the time it takes or modification A and rehydration is not necessary.

Example 2

Modification B (Hydrate) (Also Referred to as Crystalline Form B)

1 g Modification A is dissolved in a mixture of methanol/i-propyl acetate/water (5:10:0.1). The solution is evaporated to 75% volume rapidly. The solids are collected and dried at room temperature. Modification B is a crystalline hydrate.

When characterized by powder X-ray diffraction, Modification B gives the pattern shown in FIG. 2.2. The characteristic peaks are given in the Table below.

TABLE

List of characteristic PXRD peaks of Modification B

| No. | 2θ (+0.1 degree) | Intensity |
|---|---|---|
| 1 | 5.2 | 48.2 |
| 2 | 7.7 | 31.3 |
| 3 | 10.4 | 8.2 |
| 4 | 13.0 | 11.7 |
| 5 | 15.6 | 5.7 |
| 6 | 18.2 | 4.7 |
| 7 | 20.2 | 4.0 |
| 8 | 20.9 | 10.8 |
| 9 | 22.1 | 8.8 |
| 10 | 22.4 | 4.8 |
| 11 | 24.2 | 17.9 |
| 12 | 26.2 | 16.8 |
| 13 | 28.8 | 10.3 |
| 14 | 31.1 | 4.1 |
| 15 | 31.5 | 6.4 |
| 16 | 34.3 | 5.1 |
| 17 | 37.0 | 3.4 |

Modification B is characterized by a powder x-ray diffraction pattern comprising four or more 2θ values (±0.1 degree) (CuKα λ=1.5418 Å) selected from the group consisting of 5.2, 7.7, 13.0, 20.9, 24.2, 26.2 and 28.8, at a temperature of about 22° C.

Modification B is further characterized by a powder x-ray diffraction pattern comprising five or more 2θ values (±0.1 degree) (CuKα λ=1.5418 Å) selected from the group consisting of 5.2, 7.7, 13.0, 20.9, 24.2, 26.2 and 28.8, at a temperature of about 22° C.

DSC data showing the melting transitions of Modification B are displayed below. The melting point and peak area of a compound are often indicative of relative physical stability between different crystalline forms.

| Form | Onset/° C. ± 2.4 | Maximum ° C. ± 2.5 | Area (ΔH) mJ/mg |
|---|---|---|---|
| B | 280.3° C. | 256.7° C. | 16.0 |

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| B | 6.9 | 64.7° C., 82.6° C. |

Example 3

Modification C (Hydrate) (Also Referred to as Form C)

Modification A is dissolved in a mixture of ethanol/ethyl acetate (1:1) to give a clear solution. Equilibration after several hours gives a precipitate. Filtration gives Modification C.

When characterized by powder X-ray diffraction, Modification C gives the pattern shown in FIG. 2.3. The characteristic peaks are given in the Table below. The main characteristic peaks are at 5.9 and 17.0 degrees two theta (±0.1 degree) (CuKα λ=1.5418 Å) at a temperature of about 22° C.

TABLE

List of characteristic PXRD peaks of Modification C

| No. | 2θ (+0.1 degree) | Intensity |
|---|---|---|
| 1 | 5.2 | 24 |
| 2 | 5.9 | 66 |
| 3 | 7.4 | 20 |
| 4 | 8.0 | 17 |
| 5 | 9.5 | 26 |
| 6 | 10.7 | 28 |
| 7 | 11.8 | 23 |
| 8 | 13.2 | 21 |
| 9 | 14.3 | 22 |
| 10 | 15.0 | 20 |
| 11 | 16.0 | 23 |
| 12 | 17.0 | 100 |
| 13 | 18.3 | 31 |
| 14 | 19.1 | 47 |
| 15 | 19.6 | 66 |
| 16 | 20.7 | 23 |
| 17 | 21.1 | 27 |
| 18 | 21.4 | 20 |
| 19 | 22.2 | 26 |
| 20 | 22.5 | 46 |
| 21 | 22.9 | 26 |
| 22 | 23.6 | 47 |
| 23 | 24.6 | 27 |
| 24 | 24.9 | 26 |
| 25 | 26.4 | 34 |
| 26 | 26.8 | 40 |
| 27 | 27.6 | 27 |
| 28 | 28.4 | 56 |
| 29 | 28.6 | 28 |
| 30 | 29.4 | 23 |
| 31 | 30.0 | 37 |
| 32 | 30.9 | 21 |
| 33 | 32.6 | 21 |
| 34 | 33.4 | 20 |

Modification C is characterized by a powder x-ray diffraction pattern comprising four or more 2θ values (±0.1 degree) (CuKα λ=1.5418 Å) selected from the group consisting of 5.9, 17.0, 19.6, 22.5, 23.6, 28.4 and 30.0, at a temperature of about 22° C.

Modification C is further characterized by a powder x-ray diffraction pattern comprising five or more 2θ values (±0.1 degree) (CuKα λ=1.5418 Å) selected from the group consisting of 5.9, 17.0, 19.6, 22.5, 23.6, 28.4 and 30.0, at a temperature of about 22° C.

Modification C is characterized by a solid state $^{19}$F NMR spectrum comprising peaks at −67.6 and −66.0 (±0.2) ppm. The major peak in the solid state $^{19}$F NMR spectrum is at −67.6 (±0.2) ppm.

DSC data showing the melting transitions of Modification C are displayed below. The melting point and peak area of a compound are often indicative of relative physical stability between different crystalline forms.

| Form | Onset/° C. ± 2.4 | Maximum ° C. ± 2.5 | Area (ΔH) mJ/mg |
|---|---|---|---|
| C | 246.0° C. | 250.1° C. | 13.1 |

Modification A shows two endotherms at 41° C. to 67° C. that are indicative of this crystalline form. On the other hand, the water loss transition of modification C only occurs at 126° C., which indicates that water is much more tightly bound which gives this modification an advantage of being a more stable hydrate.

TABLE

Water loss as a function of temperature as measured by TG/DTA

| Form | Loss On Drying (LOD) (%) | LOD (thermal transitions) |
|---|---|---|
| A | 9.1 | 41° C., 67° C. |
| C | 2.8 | 126° C. |

Properties of Modification C
Physical Stability

Modification C is also suitable for development due to its good physical stability under ambient conditions (it does not change into another form under ambient conditions). It does not lose water until heated over 85° C., making it very stable.

On complete dehydration, its powder pattern is also largely maintained. It only converts to another modification, at high relative humidity (converting to Modification L at greater than 80% relative humidity).

Vacuum Thermogravimetric Analysis (VTGA) of Modification C

The wet solid obtained by filtering the crystallization slurry is placed in a cup placed in a cell (i.e., a small chamber) and suspended form a microbalance; vacuum is applied to the cell, and the chamber is subsequently heated. The sample mass is monitored and recorded continuously, indicating when the sample drying is complete and if moisture uptake occurs when the cell is opened to the ambient atmosphere. FIG. 4 shows the drying of Modification C in a VTGA experiment. After applying vacuum (giving 50 mbar of absolute pressure) and heating the sample in the chamber to 50° C., the sample mass decreases to a steady value after about less than 1 hour, indicating that drying is complete: upon opening the cell (pressure=1000 mbar, temperature drops to ambient value), the sample mass does not change.

In contrast to Modification A, drying modification C (see below) takes 10% less time, it takes for modification A and rehydration is not necessary.

Humidity Microbalance Analysis

A humidity microbalance analysis (VTI) of Modification C also shows that it does not lose or gain moisture when exposed at 25° C. to variations in humidity (Table below and FIG. 5).

TABLE

Sorption characteristics of Modifications C, O, N and A (at 25° C.)

| % residual humidity | Mass uptake (% water absorbed) | | | |
|---|---|---|---|---|
| | C | O | N | A |
| 0 | 0.0 | 0.0 | 0.0 | 0.0 |
| 10 | 0.0 | 0.0 | 0.1 | 3.9 |
| 50 | 0.1 | −0.5 | 0.7 | 12.0 |
| 60 | 0.2 | −0.5 | 0.9 | 12.0 |
| 70 | 0.4 | −0.5 | 1.0 | 17.3 |
| 79 | 0.8 | −0.4 | 3.7 | 17.5 |
| 90 | 12.0 | 4.3 | 18.2 | 17.4 |
| 95 | 15.6 | 13.3 | 19.1 | 17.1 |

FIG. 5, which shows mass uptake at 25° C. as a function of ambient moisture content based on humidity microbalance measurements, indicates that Modification A (Form A) adsorbs significant amounts of moisture at relative humidities as low as 10%. In contrast, Form C moisture uptake is very small, only increasing significantly at relative humidity >80%. Thus, Modification C retains a stable weight from 0% relative humidity to 80% relative humidity while Modification A loses water with decreasing humidity and gains moisture with increasing humidity. With Modification C, a rehydration step and the possible variability in water content between batches may thus be eliminated.

Thus, the present invention provides a crystalline form in the form of Modification C, which remains dry at 25° C. and at a relative humidity ranging from 0% to 80%.

For the reasons above, Modification C has been found to be particularly amenable to handling and to production of, formulation into, and analysis of the drug substance. It is a form with good physical stability and can be manufactured consistently.

Example 4

Modification D (Hydrate)

Hydration of modification B at 75% relative humidity or above converts modification B to modification D.

When characterized by powder X-ray diffraction. Modification D gives the pattern shown in FIG. 2.4. The characteristic peaks are given in the Table below.

TABLE

List of characteristic PXRD peaks of Modification D

| No. | 2θ (+0.1 degree) | Intensity |
|---|---|---|
| 1 | 5.0 | 22.0 |
| 2 | 7.5 | 13.6 |
| 3 | 10.1 | 4.3 |
| 4 | 12.6 | 5.9 |
| 5 | 15.1 | 7.2 |
| 6 | 15.8 | 3.2 |
| 7 | 16.7 | 4.3 |
| 8 | 17.6 | 4.7 |
| 9 | 19.1 | 3.5 |
| 10 | 19.7 | 3.6 |
| 11 | 20.2 | 9.8 |
| 12 | 23.6 | 3.8 |
| 13 | 25.2 | 5.0 |
| 14 | 27.8 | 3.0 |
| 15 | 30.4 | 3.3 |
| 16 | 32.9 | 2.5 |
| 17 | 35.6 | 2.8 |
| 18 | 38.3 | 2.0 |

Modification D is characterized by a powder x-ray diffraction pattern comprising four or more 2θ values (±0.1 degree) (CuKα λ=1.5418 Å) selected from the group consisting of 5.0, 7.5, 12.6, 16.7, 17.6, and 20.2, at a temperature of about 22° C.

Modification D is further characterized by a powder x-ray diffraction pattern comprising five or more 2θ values (±0.1 degree) (CuKα λ=1.5418 Å) selected from the group consisting of 5.0, 7.5, 12.6, 16.7, 17.6, and 20.2, at a temperature of about 22° C.

Modification D is characterized by a solid state $^{19}$F spectrum comprising a peak at −64.5 (±0.2) ppm.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| D | 12.4 | 84.5° C. |

Example 5

Modification E (Hydrate)

Method 1: Preparation of Modification E

From a concentration of Modification A in methanol with 5% water, i-propyl acetate is added. The solution is equilibrated for 2 hours and solids are collected.

Method 2: Preparation of Modification E

From a concentration of Modification A in methanol with 5% water at 50° C., the solution is slowly evaporated to 25% of starting volume or once solids are formed. The system is allowed to equilibrate for 2 hours then the solids are collected.

When characterized by powder X-ray diffraction, Modification E gives the pattern shown in FIG. 2.5. The characteristic peaks are given in the Table below.

TABLE

List of characteristic PXRD peaks of Modification E

| No. | 2θ (+0.1 degree) | Intensity |
|---|---|---|
| 1 | 4.8 | 20.9 |
| 2 | 7.3 | 5 |
| 3 | 9.8 | 3.4 |
| 4 | 12.2 | 4.1 |
| 5 | 15.3 | 12 |
| 6 | 15.8 | 9.3 |
| 7 | 16.9 | 13.4 |
| 8 | 17.8 | 5.7 |
| 9 | 19.3 | 4.3 |
| 10 | 19.7 | 6.6 |
| 11 | 21.0 | 5.7 |
| 12 | 21.6 | 4.5 |
| 13 | 22.7 | 9.4 |
| 14 | 23.3 | 5.3 |
| 15 | 24.7 | 14.3 |
| 16 | 27.0 | 7.1 |
| 17 | 27.1 | 7.5 |
| 18 | 29.0 | 4.1 |
| 19 | 30.7 | 4.4 |
| 20 | 31.9 | 5 |
| 21 | 34.7 | 3.8 |

Modification E is characterized by a powder x-ray diffraction pattern comprising four or more 2θ values (±0.1 degree) (CuKα λ=1.5418 Å) selected from the group consisting of 4.8, 15.8, 16.9, 19.7, 22.7, 24.7, 27.1, at a temperature of about 22° C.

Modification E is further characterized by a powder x-ray diffraction pattern comprising five or more 2θ values (±0.1 degree) (CuKα λ=1.5418 Å) selected from the group consisting of 4.8, 15.8, 16.9, 19.7, 22.7, 24.7, 27.1, at a temperature of about 22° C.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| E | 9.5 | 52.0° C., 69.6° C. |

Example 6

Modification F (Monohydrate)

i-Propyl acetate is added to a concentration of Modification A in methanol. The solution is equilibrated with slow evaporation for 24 hours and the solids collected.

When characterized by powder X-ray diffraction. Modification F gives the pattern shown in FIG. 2.6. The characteristic peaks are given in the Table below.

TABLE

List of characteristic PXRD peaks of Modification F

| No. | 2θ (±0.1 degree) | Intensity |
|---|---|---|
| 1 | 4.7 | 15.9 |
| 2 | 7.1 | 4.0 |
| 3 | 9.5 | 6.1 |
| 4 | 11.9 | 8.3 |
| 5 | 15.7 | 8.7 |
| 6 | 16.0 | 8.7 |
| 7 | 16.8 | 5.2 |
| 8 | 17.3 | 11.8 |
| 9 | 18.0 | 6.1 |
| 10 | 19.2 | 4.4 |
| 11 | 19.9 | 3.0 |
| 12 | 22.8 | 2.7 |
| 13 | 24.1 | 5.2 |
| 14 | 24.6 | 3.4 |
| 15 | 26.5 | 2.9 |
| 16 | 27.0 | 3.2 |
| 17 | 28.9 | 3.7 |
| 18 | 31.4 | 2.5 |
| 19 | 32.4 | 2.3 |
| 20 | 33.9 | 3.4 |

Modification F is characterized by a powder x-ray diffraction pattern comprising four or more 2θ values (±0.1 degree) (CuKα λ=1.5418 Å) selected from the group consisting of 4.7, 9.5, 11.9, 15.7, 16.0, 17.3, 18.0, at a temperature of about 22° C.

Modification F is further characterized by a powder x-ray diffraction pattern comprising five or more 2θ values (±0.1 degree) (CuKα λ=1.5418 Å) selected from the group consisting of 4.7, 9.5, 11.9, 15.7, 16.0, 17.3, 18.0, at a temperature of about 22° C.

Modification F is characterized by a solid state $^{19}$F NMR spectrum comprising a peak at −65.7 (±0.2) ppm.

DSC data showing the melting transitions of Modification F are displayed below. The melting point and peak area of a compound are often indicative of relative physical stability between different crystalline forms.

| Form | Onset/° C. ± 2.4 | Maximum ° C. ± 2.5 | Area (ΔH) mJ/mg |
|---|---|---|---|
| F | 251.0° C. | 255.5° C. | |

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| F | 3.5 | 90° C. |

Example 7

Modification G (Hydrate)

Hydration of Modification A at 75% relative humidity or above converts Modification A to modification G.

When characterized by powder X-ray diffraction, Modification G gives the pattern shown in FIG. 2.7. The characteristic peaks are given in the Table below.

TABLE

List of characteristic PXRD peaks of Modification G

| No. | 2θ (+0.1 degree) | Intensity |
|---|---|---|
| 1 | 4.8 | 52.5 |
| 2 | 7.1 | 24.0 |
| 3 | 9.5 | 3.2 |
| 4 | 14.3 | 10.3 |
| 5 | 15.4 | 5.0 |
| 6 | 16.6 | 9.5 |
| 7 | 17.0 | 5.6 |
| 8 | 17.6 | 11.6 |
| 9 | 18.1 | 7.0 |
| 10 | 19.1 | 7.7 |
| 11 | 23.7 | 4.6 |
| 12 | 25.6 | 3.4 |
| 13 | 26.4 | 6.0 |
| 14 | 31.2 | 3.6 |

Modification G is characterized by a powder x-ray diffraction pattern comprising four or more 2θ values (±0.1 degree) (CuKα λ=1.5418 Å) selected from the group consisting of 4.8, 7.1, 14.3, 16.6, 17.6, 18.1, 19.1, at a temperature of about 22° C.

Modification G is further characterized by a powder x-ray diffraction pattern comprising five or more 2θ values (±0.1 degree) (CuKα λ=1.5418 Å) selected from the group consisting of 4.8, 7.1, 14.3, 16.6, 17.6, 18.1, 19.1, at a temperature of about 22° C.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| G | 11.7 | 84.5° C., 95.4° C. |

Example 8

Modification H (Hydrate)

Dehydration of Modification A at 20% relative humidity or less converts Modification A to modification H.

When characterized by powder X-ray diffraction, Modification H gives the pattern shown in FIG. 2.8. The characteristic peaks are given in the Table below.

TABLE

List of characteristic PXRD peaks of Modification H

| No. | 2θ (+0.1 degree) | Intensity |
|---|---|---|
| 1 | 4.7 | 37.9 |
| 2 | 7.1 | 10.1 |
| 3 | 9.5 | 5.9 |
| 4 | 11.9 | 18.8 |
| 5 | 15.6 | 8.2 |
| 6 | 16.2 | 6.8 |
| 7 | 16.7 | 8.5 |
| 8 | 17.0 | 7.3 |
| 9 | 17.6 | 11.8 |
| 10 | 19.1 | 6.5 |
| 11 | 21.0 | 5.9 |
| 12 | 21.6 | 4.5 |
| 13 | 22.6 | 6.3 |
| 14 | 23.9 | 12.4 |
| 15 | 24.5 | 7.4 |
| 16 | 26.3 | 5.6 |
| 17 | 27.6 | 3.7 |
| 18 | 28.7 | 6.7 |
| 19 | 31.2 | 4.0 |
| 20 | 33.6 | 7.0 |

Modification H is characterized by a powder x-ray diffraction pattern comprising four or more 2θ values (±0.1 degree) (CuKα λ=1.5418 Å) selected from the group consisting of 4.7, 7.1, 11.9, 17.6, 19.1, 23.9, 33.6, at a temperature of about 22° C.

Modification H is further characterized by a powder x-ray diffraction pattern comprising five or more 2θ values (±0.1 degree) (CuKα λ=1.5418 Å) selected from the group consisting of 4.7, 7.1, 11.9, 17.6, 19.1, 23.9, 33.6, at a temperature of about 22° C.

The data listed below show the total water loss (LOD by thermogravimetry (TG)) and thermal transitions (DTA signals) show the temperature at which the water is lost.

TABLE

Water loss as a function of temperature as measured by TG/DTA.

| Form | Loss On Drying (LOD) (%) | LOD (thermal transitions) |
|---|---|---|
| H | 3 | 68.3° C. |

Example 9

Modification I (Trihydrate)

To a concentration of Modification A in methanol (with 1% water), i-propyl acetate is added. The solution is equilibrated with slow evaporation for 24 hours and the solids are collected.

When characterized by powder X-ray diffraction, Modification I gives the pattern shown in FIG. 2.9. The characteristic peaks are given in the Table below.

TABLE

List of characteristic PXRD I peaks of Modification

| No | 2θ (+0.1 degree) | Intensity |
|---|---|---|
| 1 | 4.6 | 25.1 |
| 2 | 6.9 | 8 |
| 3 | 9.2 | 5.3 |
| 4 | 11.5 | 3.8 |
| 5 | 13.8 | 3.9 |
| 6 | 15.4 | 16.9 |
| 7 | 16.3 | 17.5 |
| 8 | 16.9 | 21 |
| 9 | 17.3 | 10.3 |
| 10 | 18.4 | 6 |
| 11 | 19.2 | 5 |
| 12 | 21.1 | 3.3 |
| 13 | 21.5 | 5.4 |
| 14 | 21.8 | 4.4 |
| 15 | 22.2 | 9.7 |
| 16 | 23.0 | 6.2 |
| 17 | 24.0 | 10.1 |
| 18 | 24.8 | 3 |
| 19 | 26.0 | 4.3 |
| 20 | 26.3 | 3.8 |
| 21 | 28.2 | 4.6 |
| 22 | 30.5 | 4.4 |
| 23 | 32.0 | 6.9 |
| 24 | 33.2 | 3.5 |
| 25 | 34.9 | 4.8 |
| 26 | 36.1 | 3.8 |

Modification I is characterized by a powder x-ray diffraction pattern comprising four or more 2θ values (±0.1 degree) (CuKα λ=1.5418 Å) selected from the group consisting of 4.6, 15.4, 16.3, 16.9, 17.3, 22.2, 24.0, at a temperature of about 22° C.

Modification I is further characterized by a powder x-ray diffraction pattern comprising five or more 2θ values (±0.1 degree) (CuKα λ=1.5418 Å) selected from the group consisting of 4.6, 15.4, 16.3, 16.9, 17.3, 22.2, 24.0, at a temperature of about 22° C.

Modification I is characterized by a solid state $^{19}$F NMR spectrum comprising a peak at −65.7 (±0.2) ppm.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| I | 9.5 | 52° C., 90° C. |

Example 10

Modification J (Hydrate)

Modification A is equilibrated in ethyl acetate/methanol (10:1) with 2% water for 48 hours.

When characterized by powder X-ray diffraction, Modification J gives the pattern shown in FIG. 2.10. The characteristic peaks are given in the Table below.

TABLE

List of characteristic PXRD peaks of Modification J

| No | 2θ (+0.1 degree) | Intensity |
|---|---|---|
| 1 | 5.0 | 4.2 |
| 2 | 5.9 | 11 |
| 3 | 7.4 | 3.4 |
| 4 | 9.6 | 2.8 |
| 5 | 10.8 | 3.9 |
| 6 | 11.7 | 3.7 |
| 7 | 13.1 | 3.7 |
| 8 | 15.0 | 4.1 |
| 9 | 15.9 | 7.1 |
| 10 | 16.7 | 14.1 |
| 11 | 17.0 | 16.9 |
| 12 | 17.7 | 5.3 |
| 13 | 18.3 | 9.7 |
| 14 | 19.0 | 10.7 |
| 15 | 19.6 | 18 |
| 16 | 21.1 | 7 |
| 17 | 22.1 | 7.9 |
| 18 | 22.5 | 7.9 |
| 19 | 22.8 | 5.1 |
| 20 | 23.5 | 13.5 |
| 21 | 24.5 | 4.7 |
| 22 | 26.4 | 5 |
| 23 | 26.8 | 4.9 |
| 24 | 27.6 | 5.2 |
| 25 | 28.3 | 7.2 |
| 26 | 28.5 | 7 |
| 27 | 29.2 | 4.1 |
| 28 | 30.0 | 4.2 |
| 29 | 31.1 | 3.9 |
| 30 | 31.9 | 3.3 |
| 31 | 32.6 | 3.6 |
| 32 | 22.1 | 3.2 |

Modification J is characterized by a powder x-ray diffraction pattern comprising four or more 2θ values (±0.1 degree) CuKα λ=1.5418 Å) selected from the group consisting of 5.9, 16.7, 17.0, 18.3, 19.0, 19.6, 23.5 at a temperature of about 22° C.

Modification J is further characterized by a powder x-ray diffraction pattern comprising five or more 2θ values (±0.1 degree) (CuKα λ=1.5418 Å) selected from the group consisting of 5.9, 16.7, 17.0, 18.3, 19.0, 19.6, 23.5 at a temperature of about 22° C.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| J | 3.1 | 41° C., 120° C. |

Example 11

Modification K (Hydrate)

Modification A is dissolved in ethanol (>30 mg/ml) and THF added to give a final solvent ratio of 1.5, equilibrate is carried out for 4 hours to give Modification K.

When characterized by powder X-ray diffraction, Modification K gives the pattern shown in FIG. 2.11. The characteristic peaks are given in the Table below.

TABLE

List of characteristic PXRD peaks of Modification K

| No | 2θ (+0.1 degree) | Intensity |
|---|---|---|
| 1 | 5.9 | 7.5 |
| 2 | 6.1 | 6.6 |
| 3 | 7.0 | 3 |
| 4 | 9.3 | 3.3 |
| 5 | 10.8 | 3.3 |
| 6 | 11.8 | 2.9 |
| 7 | 13.3 | 2.7 |
| 8 | 14.0 | 4.1 |
| 9 | 15.3 | 7.4 |
| 10 | 16.1 | 6.4 |
| 11 | 16.7 | 8.6 |
| 12 | 17.0 | 9.2 |
| 13 | 18.7 | 16.4 |
| 14 | 19.0 | 7.9 |
| 15 | 19.6 | 11.6 |
| 16 | 20.1 | 7.2 |
| 17 | 21.2 | 5 |
| 18 | 22.4 | 8.2 |
| 19 | 23.3 | 3.8 |
| 20 | 23.6 | 5.5 |
| 21 | 24.6 | 3.1 |
| 22 | 25.6 | 3.2 |
| 23 | 26.4 | 3.3 |
| 24 | 26.8 | 3.1 |
| 25 | 27.7 | 4.3 |
| 26 | 28.3 | 4.2 |
| 27 | 28.6 | 3.8 |
| 28 | 28.9 | 3.2 |
| 29 | 30.0 | 2.6 |
| 30 | 31.0 | 2.6 |
| 31 | 32.5 | 2.4 |
| 32 | 34.1 | 2.3 |

Modification K is characterized by a powder x-ray diffraction pattern comprising four or more 2θ values (±0.1 degree) (CuKα λ=1.5418 Å) selected from the group consisting of 5.9, 16.7, 17.0, 18.7, 19.0, 19.6, 22.4, at a temperature of about 22° C.

Modification K is further characterized by a powder x-ray diffraction pattern comprising five or more 2θ values (±0.1 degree) (CuKα λ=1.5418 Å) selected from the group consisting of 5.9, 16.7, 17.0, 18.7, 19.0, 19.6, 22.4, at a temperature of about 22° C.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| K | 2.4 | 134.5° C. |

Modification K has low hygroscopicity.

Example 12

Modification L (Hydrate)

Hydration of Modification C at >90% relative humidity converts Modification C into modification L. The powder pattern of form Modification L shows only minor changes with drying.

When characterized by powder X-ray diffraction, Modification L gives the pattern shown in FIG. 2.12. The characteristic peaks are given in the Table below.

TABLE

List of characteristic PXRD peaks of Modification L

| No. | 2θ (+0.1 degree) | Intensity |
|---|---|---|
| 1 | 5.1 | 130.4 |
| 2 | 7.6 | 42.9 |
| 3 | 10.1 | 5.8 |
| 4 | 12.5 | 5.4 |
| 5 | 15.1 | 25.5 |
| 6 | 15.8 | 50.3 |
| 7 | 16.7 | 20.1 |
| 8 | 20.1 | 9.9 |
| 9 | 20.9 | 7.5 |
| 10 | 22.3 | 14.8 |
| 11 | 24.2 | 27.1 |
| 12 | 25.2 | 30.3 |
| 13 | 26.4 | 17.1 |

Modification L is characterized by a powder x-ray diffraction pattern comprising four or more 2θ values (±0.1 degree) (CuKα λ=1.5418 Å) selected from the group consisting of 5.1, 7.6, 15.1, 15.8, 16.7, 24.2, 25.2, at a temperature of about 22° C.

Modification L is further characterized by a powder x-ray diffraction pattern comprising five or more 2θ values (±0.1 degree) (CuKα λ=1.5418 Å) selected from the group consisting of 5.1, 7.6, 15.1, 15.8, 16.7, 24.2, 25.2, at a temperature of about 22° C.

Modification L is characterized by a solid state $^{19}F$ NMR spectrum comprising peaks at −64.7 (±0.2) ppm.

DSC data showing the melting transitions of Modification L are displayed below. The melting point and peak area of a compound are often indicative of relative physical stability between different crystalline forms.

| Form | Onset/° C. ± 2.4 | Maximum ° C. ± 2.5 | Area (ΔH) mJ/mg |
|---|---|---|---|
| L | 241.6° C. | 245.1° C. | |

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| L | 14.9% | 65° C. |

Example 13

Modification M (Anhydrous)

Completely dehydrating Modification A by heating at 60° C. yields modification M. When characterized by powder X-ray diffraction, Modification M gives the pattern shown in FIG. 2.13. The characteristic peaks are given in the Table below.

TABLE

List of characteristic PXRD peaks of Modification M

| No. | 2θ (+0.1 degree) | Intensity |
|---|---|---|
| 1 | 2.6 | 65.6 |
| 2 | 5.1 | 51.8 |
| 3 | 7.6 | 11.3 |
| 4 | 8.1 | 3.9 |
| 5 | 10.0 | 6.5 |
| 6 | 11.4 | 2.7 |
| 7 | 12.5 | 17.2 |
| 8 | 15.9 | 12.5 |
| 9 | 17.0 | 11.3 |
| 10 | 17.5 | 25.2 |
| 11 | 21.3 | 5.4 |
| 12 | 21.9 | 5.2 |
| 13 | 22.5 | 6.6 |
| 14 | 23.1 | 10.0 |
| 15 | 23.5 | 4.3 |
| 16 | 24.1 | 3.4 |
| 17 | 24.6 | 3.2 |
| 18 | 25.1 | 3.9 |
| 19 | 27.3 | 2.6 |
| 20 | 29.3 | 2.6 |

Modification M is characterized by a powder x-ray diffraction pattern comprising four or more 2θ values (±0.1 degree) CuKα λ=1.5418 Å) selected from the group consisting of 2.6, 5.1, 7.6, 12.5, 15.9, 17.0, 15.5, at a temperature of about 22° C.

Modification M is further characterized by a powder x-ray diffraction pattern comprising five or more 2θ values (±0.1 degree) (CuKα λ=1.5418 Å) selected from the group consisting of 2.6, 5.1, 7.6, 12.5, 15.9, 17.0, 15.5, at a temperature of about 22° C.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| M | 0 | None |

Example 14

Modification N (Anhydrous)

2.33 g of a mixture of Modification A and G and 15.0 g of tetrahydrofuran (THF) and 15.0 g of ethanol 200 proof are charged to a 250 ml round bottom flask. An agitator is started at about 250 rpm with positive nitrogen pressure and the system is heated 60° C. in about 15 min (water content of the hot solution was 0.27% wt by Karl Fischer determination). A slurry of Modification C slurry (in heptane) is added to the solution at 60° C. and equilibrated for about 30 min to obtain a white slurry. To the reactor, 26.0 g of heptanes are added slowly over about 2 hours. A thick white slurry is produced. The batch is then cooled to about 20° C. in about 1 hour and stirred for about 1 hour. The batch is filtered and washed with 50 g of THF. The wet cake is dried with $N_2$ for about 15 min and then in a vacuum oven at 30° C./40 cm Hg under compressed air purge overnight to yield 1.93 g (yield 83%) of white particles of modification N.

Modification N is particularly suitable for industrial scale-up. It is a crystalline anhydrous form. It also has low hygroscopicity and only starts to gain moisture at 70% relative humidity, as shown by a humidity microbalance analysis (VTI) carried out on Modification N which is exposed at 25° C. to variations in humidity (see Table in Example 3, and FIG. 6).

Thus, the present invention provides a crystalline form in the form of Modification N, which remains dry at 25° C. and at a relative humidity ranging from 0% to 70%.

When characterized by powder X-ray diffraction, Modification N gives the pattern shown in FIG. 2.14. The characteristic peaks are given in the Table below.

TABLE

List of characteristic PXRD peaks of Modification N

| No | 2θ (+0.1 degree) | Intensity |
|---|---|---|
| 1 | 6.2 | 11.7 |
| 2 | 8.3 | 13.7 |
| 3 | 13.1 | 3.7 |
| 4 | 13.5 | 4.2 |
| 5 | 15.0 | 2.8 |
| 6 | 16.6 | 62.6 |
| 7 | 18.9 | 4.4 |
| 8 | 19.6 | 34.2 |
| 9 | 21.2 | 13.9 |
| 10 | 21.6 | 5.3 |
| 11 | 21.9 | 7.5 |
| 12 | 22.8 | 2.8 |
| 13 | 24.1 | 3.2 |
| 14 | 25.0 | 9.8 |
| 15 | 25.9 | 3.3 |
| 16 | 27.5 | 2.6 |
| 17 | 28.2 | 3.1 |
| 18 | 29.4 | 7.7 |
| 19 | 30.8 | 2.4 |
| 20 | 32.2 | 3 |

Modification N is characterized by a powder x-ray diffraction pattern comprising four or more 2θ values (±0.1 degree) (CuKα λ=1.5418 Å) selected from the group consisting of 6.2, 8.3, 16.6, 19.6, 21.2, 25.0, 29.4, at a temperature of about 22° C.

Modification N is further characterized by a powder x-ray diffraction pattern comprising five or more 2θ values (±0.1 degree) (CuKα λ=1.5418 Å) selected from the group consisting of 6.2, 8.3, 16.6, 19.6, 21.2, 25.0, 29.4, at a temperature of about 22° C.

Modification N is an anhydrous form and is thus particularly suitable for industrial scale-up.

DSC data showing the melting transitions of Modification N are displayed below. The melting point and peak area of a compound are often indicative of relative physical stability between different crystalline forms.

| Form | Onset/° C. ± 2.4 | Maximum ° C. ± 2.5 | Area (ΔH) mJ/mg |
|---|---|---|---|
| N | 245.9° C. | 250.0° C. | 2.0 mJ/mg |

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| N | 0.3 | None |

Example 15

Modification O (Anhydrous)

Dried Modification A is dissolved in ethanol: the solution is then evaporated slowly with a nitrogen flow.

When characterized by powder X-ray diffraction, Modification O gives the pattern shown in FIG. 2.15. The characteristic peaks are given in the Table below.

TABLE

| No | List of characteristic PXRD peaks of Modification O 2θ (+0.1 degree) | Intensity |
|---|---|---|
| 1 | 4.3 | 17.7 |
| 2 | 6.5 | 6.9 |
| 3 | 8.7 | 10.9 |
| 4 | 10.9 | 9.6 |
| 5 | 13.1 | 4.4 |
| 6 | 13.7 | 3.5 |
| 7 | 15.2 | 18.3 |
| 8 | 17.1 | 8.2 |
| 9 | 17.8 | 26.8 |
| 10 | 18.5 | 10.3 |
| 11 | 19.1 | 16.4 |
| 12 | 19.6 | 10.9 |
| 13 | 20.4 | 6.8 |
| 14 | 21.1 | 4.7 |
| 15 | 21.4 | 6.5 |
| 16 | 22.1 | 4.8 |
| 17 | 22.5 | 4.9 |
| 18 | 23.0 | 6.5 |
| 19 | 23.9 | 5.7 |
| 20 | 24.4 | 5.1 |
| 21 | 24.7 | 6.2 |
| 22 | 25.3 | 4 |
| 23 | 26.0 | 4.9 |
| 24 | 27.2 | 5 |
| 25 | 28.3 | 3.8 |
| 26 | 29.4 | 5.2 |
| 27 | 30.8 | 3.5 |
| 28 | 31.6 | 3.7 |
| 29 | 32.3 | 3.5 |
| 30 | 33.1 | 4 |
| 31 | 33.8 | 4.3 |
| 32 | 35.1 | 3.5 |
| 33 | 36.2 | 3.2 |
| 34 | 37.1 | 3.1 |

Modification O is characterized by a powder x-ray diffraction pattern comprising four or more 2θ values (±0.1 degree) (CuKα λ=1.5418 Å) selected from the group consisting of 4.3, 8.7, 15.2, 17.8, 18.5, 19.1, 19.6, at a temperature of about 22° C.

Modification O is further characterized by a powder x-ray diffraction pattern comprising five or more 2θ values (±0.1 degree) (CuKα λ=1.5418 Å) selected from the group consisting of 4.3, 8.7, 15.2, 17.8, 18.5, 19.1, 19.6, at a temperature of about 22° C.

Modification O is characterized by a solid state $^{19}$F NMR spectrum comprising peaks at −65.9 and −64.4 (±0.2) ppm. The major peak is at −65.9 (±0.2) ppm.

Modification O is particularly suitable for industrial scale-up. It is a crystalline anhydrous form. It also has low hygroscopicity and only starts to gain moisture at 80% relative humidity, as shown by a humidity microbalance analysis (VTI) carried out on Modification O which is exposed at 25° C. to variations in humidity (see Table in Example 3, and FIG. 7).

Thus, the present invention provides a crystalline form in the form of Modification O, which remains dry at 25° C. and at a relative humidity ranging from 0% to 80%.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| O | 1.2 | None |
| P | 10.9 | 65° C. |

Example 16

Modification P (Hydrate)

Modification A is equilibrated in acetonitrile/ethanol (2:1) for 72 hours.

When characterized by powder X-ray diffraction, Modification P gives the pattern shown in FIG. 2.16. The characteristic peaks are given in the Table below.

TABLE

| No | List of characteristic PXRD peaks of Modification P 2θ (+0.1 degree) | Intensity |
|---|---|---|
| 1 | 3.9 | 3.9 |
| 2 | 4.6 | 17.8 |
| 3 | 5.8 | 2.8 |
| 4 | 6.9 | 20.8 |
| 5 | 9.1 | 14.1 |
| 6 | 11.4 | 3 |
| 7 | 13.3 | 2.8 |
| 8 | 13.7 | 2.8 |
| 9 | 14.8 | 3.3 |
| 10 | 15.2 | 3.4 |
| 18 | 21.9 | 6 |
| 19 | 22.5 | 2.4 |
| 20 | 23.3 | 5.8 |
| 21 | 23.4 | 5.7 |
| 22 | 23.9 | 4.2 |
| 23 | 24.2 | 4.3 |
| 24 | 24.5 | 3.3 |
| 25 | 25.9 | 3.7 |
| 26 | 26.4 | 3.6 |
| 27 | 27.1 | 3.4 |

Modification P is characterized by a powder x-ray diffraction pattern comprising four or more 2θ values (±0.1 degree) (CuKα λ=1.5418 Å) selected from the group consisting of 4.6, 6.9, 9.1, 17.1, 17.7, 19.3, 19.9 at a temperature of about 22° C.

Modification P is further characterized by a powder x-ray diffraction pattern comprising five or more 2θ values (±0.1 degree) (CuKα λ=1.5418 Å) selected from the group consisting of 4.6, 6.9, 9.1, 17.1, 17.7, 19.3, 19.9 at a temperature of about 22° C.

The data listed below show the total water loss (LOD by thermogravimetry (TG)) and thermal transitions (DTA signals) show the temperature at which the water is lost.

TABLE

Water loss as a function of temperature as measured by TG/DTA

| Form | Loss On Drying (LOD) (%) | LOD (thermal transitions) |
|---|---|---|
| P | 10.9 | 65° C. |

Example 17

Process for Preparing Modification C by a Slurry Method 1.1149 g of Modification A solid, 0.089 g of distilled water and 10 mL of acetonitrile are added to a glass vial. The mixture is stirred vigorously at 20° C. for 18 hours. The mixture is filtered using vacuum and the wet cake is dried in a VTGA cell at approximately 50° C. and 20 mbar for approximately 5 hours.

A stable mass is achieved after drying, but no mass change occurs upon opening the cell to the ambient environment, indicating that no moisture uptake occurred (30%-56% relative humidity) and showing clearly that Form C is not hygroscopic. The sample that is removed from the VTGA can be analyzed by powder X-ray diffraction, Karl Fisher and Gas Chromatography (GC). The PXRD analysis showed that the dried solid was highly crystalline Form C. Karl Fisher analysis indicated that the dried solid contained 3.3% water (theoretical water content for monohydrate is 3.6 wt %). The relative acetonitrile level in the dried sample, based on GC analysis, was approximately 6.9 ppm, well below the relative acetonitrile specification of 410 ppm for active pharmaceutical ingredients.

Example 18

Alternative Process for Preparing Modification C by a Slurry Method 1.2137 g of Modification A solids and 15 mL of anhydrous THF, 99.9%, are added to a glass vial. The mixture is heated to 45° C. with vigorous stirring. After slurrying at 45° C. for approximately 19 hours, the sample is filtered by vacuum and the wet cake is dried using the VTGA at approximately 50° C. and 20 mbar for approximately 5 hours.

No mass gain was observed when the dried solid was exposed to air for approximately 15 hours at 20° C. and 43-59% relative humidity. Powder X-ray diffraction analysis confirmed that the dried sample is highly crystalline Form C.

Example 19

Alternative Process for Preparing Modification C by a Slurry Method 40.2 g of the compound of formula (II) and 483.22 g isopropyl alcohol (IPA) is charged into 1 L reactor. 8.4 mL water is charged. The slurry is stirred at 20° C. for 16 hours and then filtered through a Büchner funnel. The wet cake is washed with IPA and dried at 50° C. under vacuum (25 mbar) for 16 hrs to obtain 37.8 g white powder, Hc form. Yield 94.7%

Example 20

Process for Preparing Modification C by a Recrystallisation Method 2.0 g of Modification A, 17 mL of THF and 17 mL of 200-proof ethanol are added to a jacketed 100-mL glass reactor equipped with an overhead stirrer. The mixture is heated to approximately 50° C. with vigorous agitation to obtain a clear solution. To the warm solution, 3 mL of heptanes are added. In a small glass vial, 0.02 g of seed particles (Modification C, prepared from a previous batch) are added to 1 mL of heptanes, and the slurry is sonicated for approximately 1 minute. The seed slurry is then added to the warm solution to obtain a turbid solution at 50° C. To the turbid solution, 35 mL of heptanes are added as follows. First, 5 mL of heptanes are added over a 30-min period, followed by 75-min hold. Subsequently, an additional 30 mL of heptanes are added over 1.5 hours. The resulting thick slurry is cooled to 10° C. in 50 minutes. The slurry is filtered by vacuum, and the wet cake is washed with 25 mL of anhydrous THF and dried at 65° C. and 10 mbar. Powder X-ray diffraction of the dried product indicated that it was composed of highly crystalline Form C. Based on Karl Fisher analysis, the dried solid contained 3.6% water. Relative solvent analysis by GC indicated that the dried solid contained 6.8 ppm of ethanol, 184.2 ppm of THF and 2517 ppm of heptanes. A dynamic vapor absorption experiment using the dried product confirmed that it has much lower hygroscopicity than Modification A, with a mass uptake of only 0.3% moisture from 0 to 80%, relative humidity.

Example 21

Tablet Comprising a DGAT1 Inhibitor

The following are examples of a representative pharmaceutical dosage form suitable for use in the present invention: Uncoated Tablet Comprising a DGAT1 Inhibitor, (5 Mg of Active Ingredient, Based on Free Acid of Compound 1)

| Ingredients | mg/tab |
| --- | --- |
| trans-(4-{4-[5-(6-Trifluoromethyl-pyridin-3-ylamino)-pyridin-2-yl]-phenyl}-cyclohexyl)-acetic acid, sodium salt | 5.26 |
| Microcrystalline Cellulose | 86.24 |
| Crospovidone | 7.0 |
| Colloidal silicon dioxide | 0.5 |
| Magnesium Stearate | 1.0 |
| Total weight | 100 mg |

Uncoated Tablet Comprising a DGAT1 Inhibitor (Based on 10 mg of Active Ingredient, Based on Free Acid of Compound 1)

| Ingredients | mg/tab |
| --- | --- |
| trans-(4-{4-[5-(6-Trifluoromethyl-pyridin-3-ylamino)-pyridin-2-yl]-phenyl}-cyclohexyl)-acetic acid, sodium salt | 10.51 |
| Microcrystalline Cellulose | 172.49 |
| Crospovidone | 14.0 |
| Colloidal silicon dioxide | 1.0 |
| Magnesium Stearate | 2.0 |
| Total weight | 200 mg |

Preparation Process trans-(4-{4-[5-(6-Trifluoromethyl-pyridin-3-ylamino)-pyridin-2-yl]-phenyl}-cyclohexyl)-acetic acid, sodium salt along with Microcrystalline Cellulose (partial), and Crospovidone (intragranular) are mixed in a low shear mixer. The mixed contents, along with remaining Microcrystalline Cellulose are passed through an oscillating mill equipped with a suitable screen. The screened contents are mixed in a low shear mixer for a suitable amount of time. Colloidal silicon dioxide, screened through an appropriate screen is mixed with the blend from earlier step and the contents are mixed for a suitable amount of time. Magnesium Stearate, screened through a suitable screen size is added to the preblend and mixed for a suitable amount of time. The lubricated intragranular preblend is passed through a roller compaction system for densification at the optimized parameters for feed rate, roll speed and roll force. The ribbons from the process are collected and passed through an oscillating mill equipped with a suitable screen to get the desired milled material. The milled material is then mixed with extragranular prescreened Crospovidone and mixed in a low shear mixer for a suitable amount of time. To the mixture, prescreened Magnesium Stearate is added and mixed for a suitable amount of time. The final blend is then compressed to the desired tablet weight to achieve the optimized thickness, hardness and disintegration time.

The invention claimed is:

1. A crystalline form of the sodium salt of (4-{4-[5-(6-trifluoromethyl-pyridin-3-ylamino)-pyridin-2-yl]-phenyl}-cyclohexyl)-acetic acid of formula (II)

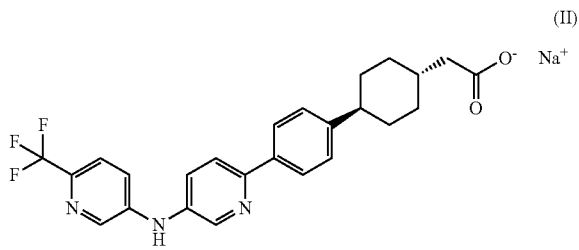

(II)

in the form of Modification B, C, D, F, I, L, N, or O.

2. A crystalline form according to claim 1 in the form of Modification C, N, or O.

3. A crystalline form according to claim 1 in the form of Modification C.

4. A crystalline form according to claim 1 which remains dry at 25° C. and at a relative humidity ranging from 0% to 70%.

5. A crystalline form according to claim 1 which remains dry at 25° C. and at a relative humidity ranging from 0% to 80%.

6. A crystalline form according to claim 1 comprising at least about 80% by weight of said Modification.

7. A crystalline form according to claim 6 comprising at least about 85% by weight of said Modification.

8. A crystalline form according to claim 1, in the form of Modification C, characterized by a powder x-ray diffraction pattern comprising four or more 2θ values (±0.1 degree) (CuKα λ=1.5418 Å) selected from the group consisting of 5.9, 17.0, 19.6, 22.5, 23.6, 28.4 and 30.0, at a temperature of about 22° C.

9. A crystalline form according to claim 8, in the form of Modification C, further characterized by a powder x-ray diffraction pattern comprising five or more 2θ values (±0.1 degree) (CuKα λ=1.5418 Å) selected from the group consisting of 5.9, 17.0, 19.6, 22.5, 23.6, 28.4 and 30.0, at a temperature of about 22° C.

10. A crystalline form according to claim 1, in the form of Modification C characterized by a solid state $^{19}$F NMR spectrum comprising a peak at −67.6 (±0.2) ppm.

11. A crystalline form according to claim 1, in the form of Modification C characterized by a melting point with an onset at 246.0° C. (±2.4) and a maximum at 250.1° C. (±2.5).

12. A crystalline form according to claim 1, in the form of Modification C characterized by a differential scanning calorimetry thermogram with an endotherm at 126° C. (±2.5).

13. A pharmaceutical composition comprising a crystalline form, according to claim 1, and one or more pharmaceutically acceptable carrier or excipient.

14. A composition according to claim 13 comprising an additional therapeutic agent.

15. A crystalline form according to claim 6 comprising at least about 90% by weight of said Modification.

16. A crystalline form according to claim 15 comprising at least about 95% by weight of said Modification.

17. A crystalline form according to claim 16 comprising at least about 99% by weight of said Modification.

* * * * *